US006749554B1

(12) United States Patent
Snow et al.

(10) Patent No.: US 6,749,554 B1
(45) Date of Patent: Jun. 15, 2004

(54) MEDICAL TOOLS AND DEVICES WITH IMPROVED ULTRASOUND VISIBILITY

(75) Inventors: Robert Allen Snow, West Chester, PA (US); Henry Wolfe, Glenmore, PA (US); Anna Rydbeck, Malmo (SE); Tore Gjorsvik, Oslo (NO); Steven Coffey, Pawcatuck, CT (US); Hakan Malmgren, Malmo (SE); Oskar Axellson, Malmo (SE)

(73) Assignee: Amersham PLC, Buckinghamshire (GB)

( * ) Notice: Subject to any disclaimer, the term of this patent is extended or adjusted under 35 U.S.C. 154(b) by 0 days.

(21) Appl. No.: 09/914,161

(22) PCT Filed: Feb. 25, 2000

(86) PCT No.: PCT/GB00/00690

§ 371 (c)(1), (2), (4) Date: Jan. 11, 2002

(87) PCT Pub. No.: WO00/51136

PCT Pub. Date: Aug. 31, 2000

Related U.S. Application Data

(60) Provisional application No. 60/121,540, filed on Feb. 25, 1999, and provisional application No. 60/130,654, filed on Apr. 23, 1999.

(30) Foreign Application Priority Data

Jun. 17, 1999 (GB) ............................................ 9914202

(51) Int. Cl.$^{7}$ ................................................ A61N 5/00

(52) U.S. Cl. ............................................ 600/3; 600/458

(58) Field of Search ................................ 600/458, 1–8, 600/439; 424/9.5–9.52

(56) References Cited

U.S. PATENT DOCUMENTS 3,351,049 A 11/1967 Lawrence

FOREIGN PATENT DOCUMENTS

| | | |
|---|---|---|
| EP | 0 386 936 A | 9/1990 |
| EP | 0 624 342 A | 11/1994 |
| WO | WO 98 18387 A | 5/1998 |
| WO | WO 98 19713 A | 5/1998 |

*Primary Examiner*—Francis J. Jaworski
(74) *Attorney, Agent, or Firm*—Robert F. Chisholm

(57) ABSTRACT

A medical or surgical device or tool that is designed to be implanted or inserted inside the human or mammalian body, having at least part of its surface coated whereby the ultrasound visibility of said device or tool in vivo is enhanced, wherein the coating comprises one or more of the following: (i) a matrix material containing a plurality of contrast enhancing elements; (ii) magnesium; (iii) a liquid or polymer which alters its ultrasound imaging properties upon elevating the temperature from ambient to physiological temperature; (iv) a liquid or polymer which alters its ultrasound imaging properties as a result of a change in pH; (v) an essentially non-polymeric bio-compatible compound which forms a discontinuous coating. Preferably the device or tool is a radioactive source for use in brachytherapy, and in particular a radioactive seed.

17 Claims, 4 Drawing Sheets

7 10 8

8 10 7

MEDICAL TOOLS AND DEVICES WITH IMPROVED ULTRASOUND VISIBILITY

This application claims the benefit of Provisional application Ser. No. 60/121,540, filed Feb. 25, 1999, and 60/130,654, filed Apr. 23, 1999.

This invention relates to radiotherapy. More particularly, it relates to radioactive sources for use in brachytherapy, and in particular to radioactive sources with improved ultrasound imaging visibility.

Brachytherapy is a general term covering medical treatment which involves placement of a radioactive source near a diseased tissue and may involve the temporary or permanent implantation or insertion of a radioactive source into the body of a patient. The radioactive source is thereby located in proximity to the area of the body which is being treated. This has the advantage that the appropriate dose of radiation may be delivered to the treatment site with relatively low dosages of radiation to surrounding or intervening healthy tissue.

Brachytherapy has been proposed for use in the treatment of a variety of conditions, including arthritis and cancer, for example breast, brain, liver and ovarian cancer and especially prostate cancer in men (see for example J. C. Blasko et al., *The Urological Clinics of North America*, 23, 633–650 (1996), and H. Ragde et al., *Cancer*, 80, 442–453 (1997)). Prostate cancer is the most common form of malignancy in men in the USA, with more than 44,000 deaths in 1995 alone. Treatment may involve the temporary implantation of a radioactive source for a calculated period, followed by its removal.

Alternatively, the radioactive source may be permanently implanted in the patient and left to decay co an inert state over a predictable time. The use of temporary or permanent implantation depends on the isotope selected and the duration and intensity of treatment required.

Permanent implants for prostate treatment comprise radioisotopes with relatively short half lives and lower energies relative to temporary sources. Examples of permanently implantable sources include iodine-125 or palladium-103 as the radioisotope. The radioisotope is generally encapsulated in a titanium casing to form a sealed radioactive source or “seed” which is then implanted. Temporary implants for the treatment of prostate cancer may involve iridium-192 as the radioisotope.

Recently, brachytherapy has also been proposed for the treatment of restenosis (for reviews see R. Waksman, *Vascular Radiotherapy Monitor*, 1998, 1, 10–18, and *MedPro Month*, January 1998, pages 26–32). Restenosis is a renarrowing of the blood vessels after initial treatment of coronary artery disease.

Coronary artery disease is a condition resulting from the narrowing or blockage of the coronary arteries, known as stenosis, which can be due to many factors including the formation of atherosclerotic plaques within the arteries. Such blockages or narrowing may be treated by mechanical removal of the plaque or by insertion of stents to hold the artery open. One of the most common forms of treatment is percutaneous transluminal coronary angioplasty (PTCA)—also known as balloon angioplasty. At present, over half a million PTCA procedures are performed annually in the USA alone. In PTCA, a catheter having an inflatable balloon at its distal end is inserted into the coronary artery and positioned at the site of the blockage or narrowing. The balloon is then inflated which leads to flattening of the plaque against the artery wall and stretching of the artery wall, resulting in enlargement of the intraluminal passage way and hence increased blood flow.

PTCA has a high initial success rate but 30–50% of patients present themselves with stenotic recurrence of the disease, i.e. restenosis, within 6 months. One treatment for restenosis which has been proposed is the use of intraluminal radiation therapy. Various isotopes including iridium-192, strontium-90, yttrium-90, phosphorous-32, rhenium-186 and rhenium-188 have been proposed for use in treating restenosis.

Conventional radioactive sources for use in brachytherapy include so-called seeds, which are sealed containers, for example of titanium or stainless steel, containing a radioisotope within a sealed chamber but permitting radiation to exit through the container/chamber walls (U.S. Pat. No. 4,323,055 and U.S. Pat. No. 3,351,049 which are incorporated by reference). Such seeds are only suitable for use with radioisotopes which emit radiation which can penetrate the chamber/container walls. Therefore, such seeds are generally used with radioisotopes which emit γ-radiation or low-energy X-rays, rather than with β-emitting radioisotopes.

In brachytherapy, it is vital to the therapeutic outcome for the medical personnel administering the treatment to know the relative position of the radioactive source in relation to the tissue to be treated, to ensure that the radiation is delivered to the correct tissue and that no localized over or under dosing occurs. Current seeds therefore typically incorporate a marker for X-ray imaging such as a radiopaque metal (e.g. silver, gold or lead). Location of the implanted seed is then achieved via X-ray imaging, which exposes the patient to an additional radiation dose. Such radiopaque markers are typically shaped so that imaging gives information on the orientation as well as location of the seed in the body, since both are necessary for accurate radiation dosimetry calculations.

Permanent implantation of brachytherapy radioactive sources for the treatment of, for example, prostate cancer may be done using an open laparotomy technique with direct visual observation of the radioactive sources and the tissue. However, the procedure is relatively invasive and often leads to undesirable side effects in the patient. An improved procedure comprising the insertion of radioactive sources transperineally into predetermined regions of the diseased prostate gland using an external template route to establish a reference point for implantation has been proposed (see for example Grimm, P. D., et al., *Atlas of the Urological Clinics of North America*, Vol. 2, No. 2, 113–125 (1994)). Commonly, these radioactive sources, for example seeds, are inserted by means of a needle device while an external depth gauge is employed with the patient in the dorsal lithotomy position.

Preferably, the insertion or implantation of a radioactive source for brachytherapy is carried out using relatively non-invasive techniques such as, for example, techniques involving needles or catheters. It is possible to calculate a location for each radioactive source which will give the desired radiation dose profile. This can be done using knowledge of the radioisotope content of each source, the dimensions of the source, an accurate knowledge of the dimensions of the tissue or tissues in relation to which the source is to be placed, plus a knowledge of the position of said tissue relative to a reference point. The dimensions of tissues and organs within the body for use in such dosage calculations may be obtained prior to placement of the radioactive source by using conventional diagnostic imaging techniques including X-ray imaging, magnetic resonance imaging (MRI) and ultrasound imaging. Ultrasound imaging has the advantage of being a real time imaging technique.

However, difficulties may arise during the radioactive source placement procedure which may adversely affect the accuracy of the placement of the source if only pre-placement images are used to guide the source placement. For example, tissue volume may change as a result of swelling or draining of fluid to and from the tissue. Tissue position can change in the patient's body relative to a selected internal or external reference point as a result of for example manipulation during surgical procedures, movement of the patient or changes in the volume of adjacent tissue. Thus, it is difficult to achieve accurate placement of sources to achieve a desired dosage profile in brachytherapy using only knowledge of tissue anatomy and position that was obtained prior to the placement procedure. Therefore, it is advantageous if real-time visualisation of both the tissue and the radioactive source can be provided. A particularly preferred imaging method due to its safety, ease of use and low cost, is ultrasound imaging.

During the placement of the radioactive sources into position, a surgeon can monitor the position of tissues such as the prostate gland using, for example, transrectal ultrasound pulse-echo imaging techniques which offer the advantage of low risk and convenience to both patient and surgeon. The surgeon can also monitor the position of the relatively large needle used in implantation procedures using ultrasound. During the implantation or insertion procedure, the location of the source may be inferred to be proximal to the tip of the needle or other device used for the procedure. However, the relative location of each separate radioactive source should be evaluated subsequent to the implantation procedure to determine if it is in a desired or undesired location and to assess the uniformity of the therapeutic dose of radiation to the tissue. Radioactive sources may migrate within the tissue following implantation. However, the relatively small size of current brachytherapy radioactive sources and the specular reflection properties of their surfaces makes them very difficult to detect by ultrasound imaging techniques, especially when they are orientated in directions other than substantially orthogonal to the incident ultrasound beam.

There is therefore a need for radioactive sources for use in brachytherapy with improved ultrasound imaging visibility.

Ultrasound reflections may be either specular (mirror-like) or scattered (diffuse). Biological tissue typically reflects ultrasound in a scattered manner, whilst metallic devices tend to be effective reflectors of ultrasound. Relatively large smooth surfaces such as those of needles used in medical procedures reflect sound waves in a specular manner.

Efforts have been made to enhance the ultrasound visibility of relatively large surgical apparatus, such as surgical needles, solid stylets and cannulae by suitable treatment of their surfaces such as roughening, scoring, etching or coating. Thus, U.S. Pat. No. 4,401,124 discloses a surgical instrument (a hollow needle device) that has a diffraction grating inscribed on the surface to enhance the reflection coefficient of the surface. Sound waves that strike the grooves are diffracted or scattered as secondary wave fronts in many directions, and a percentage of those waves are detected by the ultrasound transducer. The diffraction grating is provided for use at the leading edge of a surgical instrument for insertion within a body or for use along a surface of an object the position of which is to be monitored while in the body.

U.S. Pat. No. 5,081,997 discloses surgical instruments with sound reflective particles imbedded in a portion of the surface. The particles scatter incident sound, and a portion is detected by an ultrasound transducer.

U.S. Pat. No. 5,383,466 discloses a medical needle device that has locations coated with deposits of polymeric material containing a matrix of gas bubbles that exhibit good ultrasound reflectivity and provide good differentiation between the coating and the surrounding tissues using ultrasound imaging.

U.S. Pat. No. 4,582,061 discloses a puncturing device which has an ultrasonically coded displacement scale of acoustically reflective gaseous inclusions regularly spaced along the length of the device.

U.S. Pat. No. 4,805,628 discloses a device which is inserted or implanted for long-term residence in the body, which device is made more visible to ultrasound by providing a space in the device which has a substantially gas impermeable wall, such space being filled with a gas or mixture of gases. The invention is directed to IUD's (intrauterine devices), prosthetic devices, pacemakers, and the like.

WO 98/19713 discloses liquids and methods for applying coatings to enhance the echogenicity (i.e. ultrasound visibility) of medical devices, including needles, catheters, stents, shunts, drainage tubes, penile prostheses, urinary sphincters, dilators, introducers, angiography and angioplasty devices, pacemakers and artificial joints.

U.S. Pat. No. 5,289,831 discloses echogenic medical devices such as catheters and stents. In one embodiment, the material from which the devices are made comprises a plurality of spherically or other geometrically shaped particles in a matrix. The particles may comprise a hollow spherical space inside (column 8, line 6). Liquids, gases, gels, microencapsulants, and/or coacervates suspended in the matrix may alternatively be used either alone or in combination, so long as they form a composite with ultrasonically reflective particles in the matrix (column 8, line 23–27).

WO 98/18387 discloses medical instruments such as needles, a portion of the surface of which is covered by a carrier material that provides a matrix or support sites for a bubble generating means for generating a plurality of discrete mobile bubbles in said region to enhance ultrasound visibility of the instrument. The bubble generating means comprises a reactive substance. Upon interaction with a reactant, the substance reacts to produce bubbles. In one aspect, the gas generating material is an effervescent material such as sodium hydrogen carbonate and citric powder that is coated in an epoxy resin. Upon contacting a liquid, a quantity of mobile bubbles is produced. The bubbles are able both to migrate through the carrier material and to grow in size. The carrier can be a hydrophilic material that effectively acts to draw a small quantity of fluid from tissue to the effervescent material. Alternatively, the region to be imaged can be immersed in a fluid prior to insertion into a tissue to initiate bubble generation.

However, none of the above-mentioned prior art discloses or suggests methods for improving the ultrasound visibility of radioactive sources for use in brachytherapy, including the relatively much smaller radioactive sources or seeds for use in permanent implants, nor the need to provide improved ultrasound visibility of such sources.

According to one aspect of the present invention there is provided a radioactive source suitable for use in brachytherapy comprising a radioisotope and a suitable carrier, at least part of the surface of said source being provided with a coating whereby ultrasound visibility of the source is enhanced.

According to a further aspect of the invention there is provided a method for improving the ultrasound visibility of a radioactive source for use in brachytherapy comprising a radioisotope and a suitable carrier, the method comprising providing a coating on at least part of a surface of said source whereby ultrasound visibility of the source is enhanced.

Suitable radioisotopes are known in the art. Any radioisotope suitable for use in brachytherapy may be used in sources of the invention. Non-limiting examples include palladium-103, iodine-125, strontium-89, sulphur-35, iridium-192, yttrium-90, rhenium-186, rhenium-188, cesium-131, gold-198, thulium-170, chromium-56, arsenic-73, phosphorus-32 and mixtures thereof. Particularly preferred radioisotopes include palladium-103 and iodine-125.

Suitable carriers may comprise support materials such as plastics, graphite, zeolites, ceramics, glasses, metals, polymer matrices, ion-exchange resins or other, preferably porous materials. The support material may be in the form of a bead, wire or rod. Such support materials may be encapsulated in a hollow sealed biocompatible container, for example a metal container, to provide a sealed source or "seed", or the support material may be coated with an electroplated shell, for example a layer of a metal such as silver or nickel. Alternatively, the carrier may comprise a hollow sealed biocompatible container directly encapsulating the radioisotope without the need for a biocompatible support material. Suitable biocompatible container materials include metals or metal alloys such as titanium, gold, platinum and stainless steel; plastics such as polyesters and vinyl polymers, and polymers of polyurethane, polyethylene and poly(vinyl acetate); composites such as composites of graphite, and glass such as matrices comprising silicon oxide. The container may also be plated on the outside with a biocompatible metal, for example gold or platinum. Titanium and stainless steel are preferred metals for such containers.

Preferably, at least part of the outer surface of the source is provided with a coating. However, if the carrier comprises a hollow container, part of the inner surface of the container may be provided with a coating either in addition to or instead of the outer surface. If only the inner surface of the container is coated, the wall of the container should not be so thick that it prevents ultrasound energy from penetrating to the interior of the container and being reflected back. Coating on an inner surface is not however preferred.

The radioisotope may also be incorporated into a polymer matrix, or a plastic or ceramic composite, and/or may form part of a container wall. For example, if a metal alloy is used to form a container, then a component of the alloy may be a suitable radioisotope. If a container is made from a composite material, a component of the composite may be a suitable radioisotope.

The source should be of an overall size and dimensions suitable for its intended use. Seeds for use in the treatment of prostate cancer, for example, are typically substantially cylindrical in shape and approximately 4.5 mm long with a diameter of approximately 0.8 mm, such that they may be delivered to the treatment site using a hypodermic needle. For use in the treatment of restenosis, a source should be of suitable dimensions to be inserted inside a coronary artery, for example with a length of about 10 mm and a diameter of about 1 mm, preferably a length of about 5 mm and a diameter of about 0.8 mm, and most preferably with a length of about 3 mm and a diameter of about 0.6 mm. Sources for use in the treatment of restenosis are typically delivered to the treatment site using conventional catheter methodology. The sources of the invention may also be substantially spherical in shape.

The sources of the invention may be used as permanent implants or for temporary insertion into a patient. The choice of radioisotope and type of source, plus the method of treatment used, depends in part on the condition to be treated.

Optionally, the outer surface of the coating may be roughened, i.e., the coating material may be other than smooth in its surface features. Such roughening may further enhance the ultrasound visibility of the source.

The coating material should be biocompatible. Optionally, the coating material may also be bioabsorbable. The coating should be thick enough such that the ultrasound visibility of the source is enhanced, but not so thick that the coated source cannot be delivered using conventional delivery methods and devices. For example, if the source is a radioactive seed, the overall diameter of the coated seed is preferably less than the internal diameter of an 18 gauge needle (0.838 mm or 0.0330 inches). Thus, for example, if a radioactive seed has a diameter of 0.8 mm then the maximum thickness of any coating will be 19 $\mu$m if the coated seed is to be delivered using an 18 gauge needle with a nominal inner diameter of 0.838 mm. The coating is preferably between about 1 and 100 $\mu$m in thickness, more preferably between about 5 and 50 $\mu$m in thickness.

The coating can be of uniform or non-uniform thickness. The coating may cover the whole outer surface of the source or only part of the surface. For example, the coating may be present as a band around the centre of the source, or may be localized at the ends of a nonspherical source. Preferably, the coating is present in a spiral configuration on the outer surface of the source.

The coating material may comprise a matrix material which contains a plurality of contrast enhancing elements such as bubbles or microbubbles of gas or a precursor to a gas, or ultrasound-reflecting particles, for example hollow or solid particles, either uniformly or non-uniformly distributed in the matrix. The contrast enhancing elements should contribute to enhanced ultrasound visibility and detectability of the source.

The contrast enhancing elements are preferably about 0.1–500 $\mu$m in size (i.e. in diameter, length or width), more preferably 1–50 $\mu$m and most preferably 5–10 $\mu$m in size.

The matrix material may be a polymer. Examples of suitable polymers include polyurethanes, polyethylene, polypropylene, poly(ethylene-co-vinyl acetate) including partially hydrolyzed poly(ethylene-co-vinyl acetate), poly (ethylene-co-vinyl alcohol), polysilicones, polybutylene and isomeric polybutylene such as polyisobutylene, polyisoprene, halogenated rubbers, halogenated elastomers such as polyvinyl chloride, polymers and copolymers of vinyl-alkylenes, polymeric ethylene oxides, polyethers, polyacrylates such as poly(hydroxyethyl acrylate), paints such as Chemglaze A276, S13GLO, YB-71, and D-11, which are the paints used on the United States space shuttle, polyepoxides such as polymers of glycidol, polyacrylamides, polypeptides, polyvinylpyrrolidone, gelatin and the like.

Mixtures of polymers including compatible polymers and phase separating incompatible polymers may be used in the coating materials. Examples of suitable film forming polymers can be found in WO 98/19713, which is incorporated by reference.

A suitable coating material for the radioactive sources of the invention is available under the trade name ECHO-COAT™ from STS Biopolymers, Inc. of Henrietta, N.Y. state, U.S.A. Such coatings have been applied to other medical devices such as needles to enhance ultrasound visibility. (Advances in Ultrasound Imaging, PR Newswire, Feb. 24, 1998, pp0224, NYTU089 which is incorporated by reference).

Suitable coating materials for use in the invention also include matrix materials such as a fused or melted amino acid (for example, glycine, serine, threonine, cysteine, tyrosine, asparagine, glutamine, aspartic acid, glutamic acid, lysine, arginine, histidine, alanine, hydroxyproline, isoleucine, leucine, methionine, norleucine, ornithine, phenylalanine, proline, pyroglutamic acid, sarcosine, tryptophan, valine, and naturally occurring derivatives thereof), glucuronic acid, gluconic acid, glucaric acid, galacturonic acid, mannuronic acid, glucosamine, galactosamine, and neuraminic acid, and naturally occurring derivatives thereof, or a fused sugar (for example, erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, and the like), wherein exemplary fused monosaccharides may have six carbon atoms (for example, allose, altrose, glucose, mannose, gulose, idose, galactose, talose, fructose, psicose, and tagatose), five carbon atoms (for example, ribose, arabinose, xylose, lyxose, ribulose and xylulose), or four carbon atoms (for example, erythrose, threose and erythrulose), or fused mixtures of these materials.

In the case of an insoluble coating, the matrix and particles would stay with the source even after implantation or insertion of the source into a patient's body. In the case of a soluble or dissolving coating, the matrix should be biocompatible, and the particles should be biocompatible and preferably eliminatable, degradable or soluble.

A polymer coating may be susceptible to degradation by radiation when coated on the surface of a radioactive source. Radiation includes x-ray radiation, γ-particle radiation, β-particle radiation, α-particle radiation, ultraviolet radiation and visible light radiation. Polymers used as coatings for radioactive sources may be made more resistant to the effects of radiation by including antioxidant materials, free radical inhibitors or free radical chain transfer agents in the coating.

Suitable antioxidants are known in the art and include sodium bisulfate, ascorbic acid, esters of ascorbic acid such as ascorbyl palmitate and stearate, vitamin E, vitamin E acetate, vitamin E palmitate as well as other esters of tocopherol, sodium sulfite, sodium metabisulfite, cysteine, cysteine hydrochloride, thioglycolic acid, butylated hydroxyanisole, butylated hydroxytoluene, lecithin, propyl gallate, tetramethylpiperidine and similar bisdialkylmethyleneamine-containing compounds, pyrogallol, polyhydroxy phenolic compounds with ortho or para hydroxy groups, hydroquinones, tetrahydroxydimethyl biphenyl, nordihydroguaiaretic acid, tyrosine, sarcosine, quinoline, nicotinic acid, thiourea, thioacetic acid and thioacetic acid esters, flame retardants, and brominated alkyls. Additionally, iodinated x-ray contrast agents and iodinated aromatic materials may be added to the coating to enhance the stability of the polymer to radiation induced degradation.

Plasticizers such as vitamin E palmitate or acetate and one or more phthalate esters may also be added to the coating to help maintain flexibility.

Suitable contrast enhancing particles include particles of metal (for example titanium or aluminium), glass, silica, iron oxide, sand, clays, plastics such as teflon, carbon particles such as graphite, porous uniformly-sized non-aggregated particles as described in U.S. Pat. No. 5,741,522 and U.S. Pat. No. 5,776,496 which are incorporated by reference, hollow microcapsules or solid microspheres such as those disclosed in U.S. Pat. No. 5,648,095 which is incorporated by reference, and microspheres of a fused sugar, a fused amino acid or of PEG.

Examples of other such particles are disclosed in U.S. Pat. No. 5,289,831, U.S. Pat. No. 5,081,997 and EP-A 0,500,023 which are incorporated by reference.

The contrast enhancing elements may be uniformly distributed throughout the coating material, or they may be localized in certain areas. For example they may be located at interfaces within the coating or be present at the surface of the coating.

The contrast enhancing elements for use in the coatings of the invention also include bubbles or microbubbles of gases such as air, carbon dioxide, fluorocarbons, freons, nitrogen etc. U.S. Pat. No. 5,333,613 which is incorporated by reference, discloses methods to produce microbubble ultrasound contrast agents. Bubbles may be introduced into the coating by sonication of the molten coating material in a suitable gas atmosphere prior to coating of the source, then coating the source and cooling to solidify the coating material and so freeze bubbles of gas inside the coating.

Alternatively, if the coating material comprises a foam, bubbles of gas may be trapped in the coating during formation of the foam. Suitable foams include polyurethane foams which form on contact with water. Other suitable foams may be formed by reaction of an effervescent salt such as a benzene diazonium carboxylate, (which can generate nitrogen and carbon dioxide), or an anhydrous mixture of citric acid and sodium bicarbonate, (which can be used to produce carbon dioxide in water), with water or by reaction of, for example, a bicarbonate salt with acid, in the presence of an elastomer which can trap the generated gas. Other foams may be obtained by coating the source with a film comprising a low boiling liquid such as perfluorooctyl bromide in the form of an emulsion coating, and then heating the coating to produce a gas from the liquid, so forming a foam.

A typical reaction for the generation of a polyurethane foam is shown in Scheme 1 below.

Scheme 1

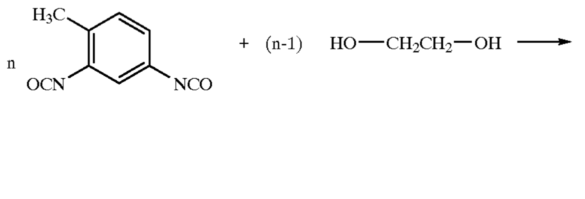

-continued

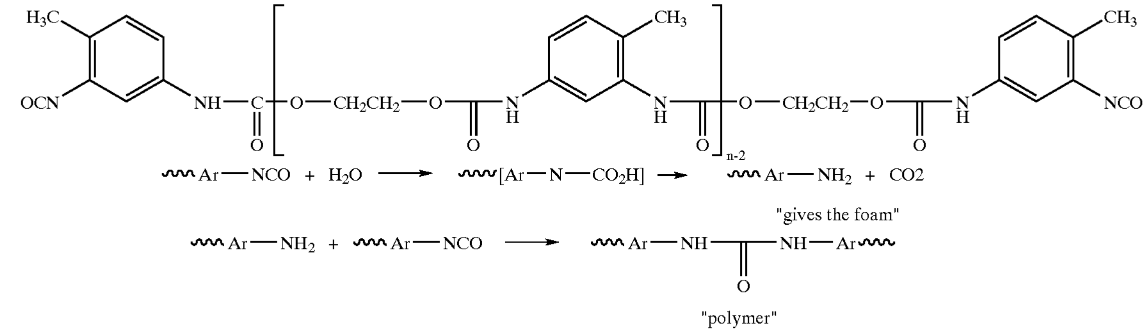

In order to produce a foam coating, a source may be coated with foam precursors and a foam generated on exposure to suitable conditions, for example on exposure to water. Possible foam precursors include suitable prepolymers, for example prepolymers comprising isocyanate groups.

For example, a source may be coated with a microlayer/microfilm of a diisocyanate that is partially polymerized with a dihydric alcohol such as ethylene glycol. When exposed to water, such a layer or film may react and generate carbon dioxide gas, so forming a polyurethane foam around the carrier. The carbon dioxide will be trapped in the foam. Such polyurethane foams should be inert to the body and not degrade with time. The polymer polyurethane is used in other medical in-vivo applications such as polyurethane-coated stents (WO 98/19713), indicating that the polymer should be bicompatible. Optionally, the polymer can be crosslinked, for example, or include a triisocyanate or polyisocyanate in the microlayer or in the microfilm.

Exposure of the film or layer to water may occur inside a patient's body when the source is administered to a patient. Preferably however, the source may be covered with a polyurethane foam prior to administration into the body. This may give better control of the reaction conditions and helps ensure that a sufficient and even coating is achieved.

An isocyanate group can react with water to form $CO_2$ and an amine. The amine can react with another isocyanate group to form a urea. The reaction of diamines with diisocyanate has been described by S. R. Sandler and W. Karo in Polymer Synthesis, Volume I, Chapter 7, Academic Press, New York, 1974, pp 189–191 which is incorporated herein by reference. Urea groups can also react with isocyanate groups to form biuret groups. Suitable isocyanate-containing prepolymer materials include monoisocyanates, diisocyanates, triisocyanates, polyisocyanates, oligomeric isocyanates, and prepolymers, oligomers or co-polymers containing pendant or terminal isocyanate groups.

Monoisocyanate-containing materials can be useful in the generation of gases and can act as polymer chain termination agents in the formation of polyurethanes and polyureas. A polymer layer can be formed from one or more isocyanate-containing prepolymer materials. Aliphatic and aromatic monoisocyanate-containing materials can also be polymerized, for example with the aid of an anionic catalyst to form 1-nylons. Such reactions are described by S. R. Sandler and W. Karo in Polymer Synthesis, Volume III, Chapter 8, Academic Press, New York, 1980.

Examples of suitable diisocyanate-containing prepolymer materials for the formation of polymers such as polyureas include toluene diisocyanate (CAS Registry No. 26471-62-5); 2,4-toluene diisocyanate (CAS Registry No. 584-84-9); 2,6-toluene diisocyanate (CAS Registry No. 91-08-7); 2,5-toluene diisocyanate (CAS Registry No. 614-90-4) 3,3'-dimethoxy-benzidine-4,4'-diisocyanate (CAS Registry No. 91-93-0); p,p'-diphenylmethane diisocyanate (CAS Registry No. 101-68-8); 4,4'-diphenylmethane diisocyanate (CAS Registry No. 26447-40-5); trans-1,4-cyclohexane diisocyanate (CAS Registry No. 7517-76-2); isophorone diisocyanate (CAS Registry No. 4098-71-9); 3,3',5,5'-tetraethyldiphenyl-methane-4,4'-diisocyanate (CAS Registry No. 105442-35-1); 3,3'-bitolylene 4,4'-diisocyanate (CAS Registry No. 91-97-4); m-phenylene diisocyanate (CAS Registry No. 123-61-5); p-phenylene diisocyanate (CAS Registry No. 104-49-4); dicyclohexylmethane-4,4'-diisocyanate (CAS Registry No. 5124-30-1); m-xylylene diisocyanate (CAS Registry No. 3634-83-1); 3,3'-dichlorodiphenyl 4,4'-diisocyanate (CAS Registry No. 5331-87-3); 1,2,4,5-tetramethyl-3,6-diisocyanate (CAS Registry No. 719-61-9); 5-chloro-2,4-toluene diisocyanate (CAS Registry No. 15166-26-4); methane diisocyanate (CAS Registry No. 4747-90-4); hexamethylene diisocyanate (CAS Registry No. 822-06-0); 2,4,4-trimethylhexamethylene diisocyanate (CAS Registry No. 15646-96-5); trimethylhexamethylene diisocyanate (CAS Registry No. 28679-16-5); octamethylene diisocyanate (CAS Registry No. 10124-86-4); tetramethylene diisocyanate (CAS Registry No. 4538-37-8); 1,3-bis(1-isocyanato-1-methylethyl)benzene (CAS Registry No. 2778-42-9); 3,3'-dimethyldiphenylmethane-4,4'-diisocyanate (CAS Registry No. 139-25-3); 4-bromo-6-methyl-1,3-phenylene diisocyanate (CAS Registry No. 55206-98-9); and alpha,alpha-dimethyl-alpha, 4-phenethyl diisocyanate.

Preferred isocyanate-containing prepolymer materials include hexamethylene diisocyanate, tetramethylene diisocyanate, toluene diisocyanate and substitutional isomers of toluene diisocyanate, trans-1,4-cyclohexane diisocyanate, 4,4'-diphenylmethane diisocyanate, dicyclohexylmethane-4,4'-diisocyanate, and isophorone diisocyanate.

A suitable triisocyanate-containing prepolymer material is triphenylmethane-4,4',4"-triisocyanate (CAS Registry No. 2422-91-5), which is sometimes known as Desmodur® RE.

Also suitable for the formation of polymers are isocyanate-containing prepolymer materials such as oligomeric and polymeric materials that comprise isocyanate functional groups. These also include oligomers that comprise end-capped isocyanate groups. Examples of useful oligomeric and polymeric compounds that contain isocyanate groups include poly(tolylene 2,4-diisocyanate) (CAS Registry No. 26006-20-2, sometimes known as Desmodur® IL) which is soluble in butyl acetate as a solvent for coating purposes; tolylene 2,4-diisocyanate terminated poly (propylene glycol) (CAS Registry No. 9057-91-4); tolylene 2,4-diisocyanate terminated poly(ethylene adipate) (CAS Registry No. 9019-92-5); tolylene 2,4-diisocyanate terminated poly(1,4-butanediol) (CAS Registry No. 9069-50-5); isophorone diisocyanate terminated poly(propylene glycol) (CAS Registry No. 39323-37-0); poly(1,4-phenylene diisocyanate-co-poly(1,4-butanediol) (CAS Registry No. 89339-41-3); poly(isophorone diisocyanate)(CAS Registry No. 53880-05-0, sometimes known as Desmodur® Z4370) which is soluble in propylene glycol methyl ether acetate/xylene (1:1) for coating purposes; poly(hexamethylene diisocyanate) (CAS Registry No. 28182-81-2, sometimes known as Desmodur® N-100, Desmodur® N-3200 or Desmodur® N-3300); isophorone diisocyanate terminated poly(1,4-butanediol) (CAS Registry No. 39323-37-0); triphenylolmethane triglycidyl ether adduct with 2,6-tolylene diisocyanate (CAS Registry No. 106253-69-4); poly(toluene diisocyanate); isophorone diisocyanate terminated poly(neopentyl glycol adipate); modified poly(4,4'-diphenylmethane diisocyanate) (which is sometimes known as Desmodur® MP-225 and also Desmodur® MP-100); the adduct of toluene diisocyanate and polyol (which is sometimes known as Desmodur® L-75N); trimethylolpropane-co-xylylene diisocyanate; trimethylolpropane-co-tolylene diisocyanate; and trimethylolpropane-co-hexahydroxylylene diisocyanate.

Preferred isocyanate-containing prepolymer materials include poly(tolylene 2,4-diisocyanate), tolylene 2,4-diisocyanate terminated poly(propylene glycol), tolylene 2,4-diisocyanate terminated poly(1,4-butanediol), and Desmodur® prepolymers.

In a further embodiment of the invention, bubbles may be formed in the coating material as a result of coating the source with a suspension of powdered or ground particulates of frozen or solidified suspensions of gas bubbles or gas microbubbles.

U.S. Pat. No. 5,830,435 which is incorporated by reference discloses a method for preparing frozen suspensions of gas microbubbles immobilised in a frozen aqueous medium. The bubbles are bound by an evanescent envelope or a tangible member.

For example, the frozen suspensions may be suspended in a solution of a matrix polymer or a matrix prepolymer that is dissolved in a coating solvent. Alternatively, the domains may be placed in the matrix as a result of coating using particulates of a frozen solution of a gas such as a pressurized gas. Such solutions may be formed by dissolving a gas in a liquid such as an aqueous liquid to form a solution of a gas-in-a-liquid, and then freezing the gas-in-liquid solution to entrap the gas as a gas-in-solid solution. The gas-in-solid solution may then be ground at a temperature below the freezing point of the gas-in-solid solution to form a particulate or powder of about 5 to 100 $\mu$m in diameter that can be suspended in a coating solvent which contains a matrix material.

Preferably, the frozen solutions comprise frozen aqueous solutions, and the frozen suspensions comprise frozen aqueous suspensions.

The suspension of frozen bubbles or microbubbles or suspension of a frozen solution of gas may be coated onto a carrier in a solution of a matrix polymer or pre-polymer in an organic solvent at a temperature below the melting point of the frozen suspension or solution. Preferably, the solvent for the coating step is a halogenated material such as methylene chloride or chloroform, or another solvent that can dissolve and coat the matrix polymer at a temperature low enough to maintain the frozen component as a solid or prevent the frozen component from rapidly dissolving.

Preferably the coating solvent does not readily dissolve or melt the frozen component. The frozen component such as a frozen aqueous suspension or aqueous solution may be insoluble or immiscible in the coating solvent or it may be substantially insoluble or imiscible in the coating solvent. It can be substantially soluble or miscible in the coating solvent when present as a liquid, but it should be substantially insoluble or immiscible in the coating solvent when present as a frozen solid. The rate of dissolution of the frozen component should be slow relative to the coating and drying time of the matrix polymer. The coating solvent may then be pumped away at low temperatures under reduced pressure to leave a coating of polymer containing domains of frozen bubbles.

Optionally, besides coating and drying of a matrix polymer in the presence of the frozen component from a solution of a coating solvent, other matrix coating and forming methods can be used in the presence of the frozen component. These include, for example, coating and drying a solution of a matrix prepolymer. A prepolymer such as a diisocyanate can form a polyurethane in the presence of water. Water may come from the melting or partial melting of a frozen aqueous suspension of bubbles or from the melting or partial melting of a frozen solution of gas.

Alternatively, a matrix can be formed by coating and drying a solution of a photopolymerizable matrix prepolymer plus an appropriate photosensitizer and irradiating the prepolymer to polymerize it. The prepolymer can comprise one or more than one of a photopolymerizeable monomer or a photopolymerizeable oligomer. For example, a combination of one or more alkyl acrylates and ethylene glycol diacrylate and a photosensitizer such as a coumarin triplet sensitizer can be used. The combination can be polymerized in the presence of light or external radiation or internal radiation (such as radiation from a radioactive seed). Additionally, a silanol prepolymer may be used. A silanol can form a siloxane-linked matrix. A bis-silanol can form a polysiloxane matrix. Chlorosilyl-groups can hydrolyze to form hydroxysilyl groups (silanols) in the presence of water, especially water buffered with an acid acceptor.

The frozen solution or suspension can be thawed after the matrix is formed to mobilize the bubbles in the domains in the matrix. The bubbles in the many regions in the coated matrix may enhance the overall echogenicity of the coated seed.

Optionally, the coated sources can be freeze dried to remove water. After storage, the water content can then be restored by hydration, for example by dipping the source in water prior to use, or by lavage before, during or immediately after implantation, or by rehydration from fluid in tissue after implantation. Rehydration can be done most easily if a water or water vapor permeable matrix such as poly(ethylene-co-vinyl acetate-co-vinyl) alcohol is used.

Optionally, the coatings of the invention may be provided with a top-coat to provide additional desired properties such as smoothness, low coefficient of friction for insertion of the coated source via a syringe needle or the like, hydrophilicity (e.g., to act as a wick or wetting agent during rehydration of freeze-dried domains), a hardened outer surface layer, and the like.

Adhesion of a coating to the surface of a source, for example a seed, may be improved by cleaning the surface prior to the coating step to remove grease and other non-adhering materials. Adhesion may also be improved by application of a primer coat layer on the surface of the source prior to the application of the coating material. A primer coat should adhere both to the source, such as to a surface of a seed, and also to a coating layer coated on the primer coat. Use of a primer coating is preferred when the coating layer does not adhere to the source surface to a useful degree.

The surface of the source may be activated for binding to a primer layer or for binding directly to a polymer coating, for example a polymer coating derived from an isocyanate-containing prepolymer. For example, if the source is made of titanium, the titanium may be activated by rutilization of its surface to form a coherent layer of titanium oxide thereon.

A suitable method for rutilization of the surface of a titanium source, for example a seed, comprises immersing the source in an alkaline solution, for example a sodium hydroxide solution, which also comprises a peroxide such as hydrogen peroxide for a suitable period of time, for example up to about 20 minutes. The temperature of the alkaline solution may be between ambient temperature and about 70° C. A suitable solvent is water. The concentration of the alkaline solution may be up to about 0.5 normal. The concentration of the peroxide may be up to about 10% by volume. After such treatment, which may leave the surface darkened due to the presence of a titanium oxide layer, the source may be washed with hot water for about ten minutes, dried with warm dry air, and then a suitable coating may be applied.

Optionally, a source can be anodized to prime the surface, for example by applying an increasing voltage of up to about 20 V to a titanium seed for up to about 20 minutes while the seed is immersed in an alkaline bath that optionally contains hydrogen peroxide.

Other suitable methods that may be used for activation of a surface of a metal seed prior to coating with an ultrasound visibility enhancing layer include the surface treatment disclosed in U.S. Pat. No. 5,869,140, hereby incorporated by reference, that employs a stabilized alkoxyzirconium organometallic salt such as tetrapropoxyzirconium and a coupling agent such as 3-glycidoxypropyltrimethoxysilane in the presence of acetic acid and water to form a sol-gel film covalently bonded on a metal surface.

A primer coating should adhere to the surface of the seed or to an activated surface of a seed. A primer coating may comprise a composition of one or more compounds. Examples of useful primer compositions include copolymers of ethylene and acrylic acid, for example poly (ethylene-co-acrylic acid) (CAS Registry No. 9010-77-9), poly(ethylene-co-propylene-co-acrylic acid) (CAS Registry No. 26125-51-9), and poly(ethylene-co-methyl acrylate-co-acrylic acid) (CAS Registry No. 41525-41-1). Poly (ethylene-co-acrylic acid) can be coated as a warm solution in toluene and cyclohexanone.

Optionally, a primer coat may comprise one or more isocyanate-containing prepolymer materials. Preferably such materials are compatible with the primer materials and do not rapidly phase separate from the primer polymer domains in the absence of solvent.

A primer coating may be applied to the surface of a source by conventional coating techniques that include dip-coating, brush coating, curtain coating, roller coating, and spray coating of a solution of one or more primer compositions. A primer coating may also be applied as melt coating of a solventless polymer composition.

A primer coating can also be formed by first coating a surface of a source with a prepolymer composition comprising one or more polymerizable compounds and then polymerizing the composition to form a coating. Suitable polymerizable compounds include vinyl monomers, olefinic materials, oligomers containing polymerizable groups, reactive isocyanate-containing materials, and the like. Optionally, a prepolymer composition may also comprise one or more additional components such as a polymerized primer composition; a binder such as polyvinylpyrolidone; a water soluble salt such as sodium chloride or sodium bicarbonate; a free radical precursor such as a thermally labile peroxide, for example benzoyl peroxide; a thermally labile azobis compound such as 4,4-azobis(4-cyanovaleric acid), 1,1'-azobis(cyclohexanecarbonitrile), and the like; a photosensitizer such as a coumarin useful in photosensitized polymerizations; a dye such as a fluorescent dye; or a singlet oxygen sensitizer such as methylene blue that is useful for the light-initiated conversion of triplet oxygen to singlet oxygen.

Other suitable primer compositions include compositions comprising shellac which can be applied in a solvent such as ethanol or denatured ethanol and compositions comprising cellulose esters such as cellulose acetate and cellulose acetate butyrate which are soluble in cyclohexanone and ethyl acetate. Another suitable primer composition comprises epoxide-containing organosilanes such as gamma-glycidoxypropyl-trimethoxysilane that can be applied, for example to a titanium surface that has been treated with an aqueous silicate solution as described in U.S. Pat. No. 5,660,884 which is hereby incorporated by reference. Other suitable primer compositions comprise a peroxide curable resin based on polyethylene or ethylene-alpha-olefin copolymer or ethylene-alpha-olefin-butadiene terpolymer. Such compositions may also comprise a peroxide such as benzoyl peroxide.

The reactive components of a prepolymer composition can be polymerized and cured, for example by radiation initiated polymerization, by thermal initiated polymerization, by light initiated polymerization, by water induced isocyanate polymerization, by crosslinking reactions and chain transfer reactions, and the like.

A primer coat may also be cured as a result of heat treatment of a coated layer. This can initiate a crosslinking reaction in the coating. Optionally, other well known methods of curing or crosslinking a primer can be used. These include photocrosslinking, radiation induced radical formation and subsequent crosslinking, application of a bifunction or polyfunctional reactive species such as a diglycidyl ether, for example, butanediol diglycidyl ether, and application of sulfur at the time of coating followed by vulcanization.

A primer layer can comprise one or more primer compositions that can be separately or simultaneously cured.

Suitable coating or application methods for formation of a primer and/or a coating layer are known in the art. They include dipping or rolling the source in a solution, mixture or melt of the coating material, spray coating, brush coating or painting. A source may also be coated with a suitable pre-polymer which is then polymerised in situ, for example by exposure to water or light. WO98/19713 which is hereby incorporated by reference discloses suitable coating methods.

If spray coating is used, a preferred method comprises rotation of a source in the path of a sprayed coating composition. This can be accomplished by rotation of the source, preferably substantially along the long axis of the source, in the path of the spray. Rotation should be fast enough to provide a substantially uniform coating on the source but slow enough to prevent substantial removal of the coating from the source, for example by splattering caused by high rotational forces. This can also be accomplished by rotation of the source of the spray around the source, preferably substantially perpendicular to an axis of the source, and preferably in a horizontal plane.

Concentration of coating materials in a spray coating can range from about 1% to about 50% of the solution to be sprayed. Concentration of materials in a dip coating can range from about 1% to about 90%. A preferred concentration range for isocyanate-containing coating materials is from 1% to about 25% of the solution. For solutions of coating materials, optimum coating concentrations can be found empirically and will depend on the coating method used, the volatility of the solvent system used, the temperature of application, and the viscosity of the solution to be coated.

Alternatively, if the carrier comprises a hollow sealed container encapsulating a radioisotope, either with or without a support material, ultrasound visibility of the source may be enhanced by inclusion of a suitable echogenic "tag" within the sealed container. Suitable tags include microballoons of gas in the form of an elastomeric matrix containing the microballoons, and optionally also containing the radionuclide.

Such tags may be used in addition to or instead of a surface coating of the source to enhance ultrasound visibility.

If the coating material is porous, soluble or swellable by water, it may comprise particles of a gas precursor which will liberate a gas on contact with a gas generating substance such as acid in water. One suitable gas precursor comprises sodium hydrogen carbonate ($NaHCO_3$). Suitable swellable polymers include EVA, i.e. poly(ethylene-co-vinyl acetate), and partially hydrolized EVA.

Alternatively, even if the coating material is not porous, soluble or swellable, its outer surface may still comprise particles of a gas precursor such as $NaHCO_3$ which will liberate a gas on contact with water. The more acidic the water, the faster the liberation of gas.

When $NaHCO_3$ comes into contact with water, for example on insertion of a source into a patient's body or by addition of water at acidic pH at the time of insertion or shortly thereafter, the following reaction will occur:

$$NaHCO_3+H_3O^+\rightarrow Na^++2H_2O+CO_2$$

This will create small bubbles of carbon dioxide on the surface of the source. These bubbles can enhance the visibility of the source to ultrasound.

The $CO_2$ will eventually be absorbed by the surrounding body fluids. A slight rise of the pH in the immediate surroundings will occur, but the amounts of $NaHCO_3$ needed are so small that the pH effect can be negligible.

Alternatively, a gas generating substance such as a solid acid, for example an organic acid such as citric acid, oxalic acid, tartaric acid or aspartic acid, may be mixed or blended with, adsorbed onto or applied to the surface of a coating material. If a solution of a bicarbonate or carbonate salt in, for example, water for injection, is administered to or adjacent to a coated seed, then bubbles of gas can form from reaction of the bicarbonate or carbonate and the acid. The bubbles can render the seed more visible to ultrasound.

Other suitable gas generating substances include other carbonate or bicarbonate salts, dry mixtures comprising powdered carbonate or bicarbonate salts, e.g. $NaHCO_3$, and an organic acid such as oxalic, citric, tartaric or aspartic acid, or droplets of perfluorooctyl bromide optionally in a liposome or surfactant bubble (e.g. F108, F68 or albumin). When exposed to suitable conditions, for example to water-containing fluids such as blood or plasma, or by administration or flushing of the source with a water-containing fluid such as water for injection or saline solution, gas bubbles can be generated proximal to the source. Ultrasound visibility can be improved by the presence of gas bubbles in, on or about the surface of the source.

As a further feature of the invention there is provided a delivery device suitable for delivery of a radioactive source for use in brachytherapy and an ultrasound contrast enhancing agent to a site to be treated within a patient, said delivery device comprising a needle for delivery of the radioactive source and a tube associated therewith for delivery of the contrast enhancing agent.

In a preferred embodiment the tube will be integrally formed with the delivery device or forms part of the operating mechanism of it. It will desirably be substantially parallel with the needle. As used herein, substantially parallel should be taken to include situations wherein the needle and the tube are substantially co-axial.

Preferably, the tube is connected to a reservoir, for example a syringe or other container, suitable for holding an ultrasound or other contrast enhancing agent.

In one embodiment of the device, the tube for delivery of the contrast enhancing agent is attached to the outside of the needle. Alternatively, a tube may be provided inside the needle, as long as it does not hinder passage of a radioactive source through the needle. In a further embodiment, the plunger used to push a radioactive source through the needle may be provided with a tube through which the contrast enhancing agent can pass to the site of insertion of the source. In such a device, the plunger will fulfil the dual roles of pushing the source through the needle and delivery of the contrast enhancing agent to the site of the source within the patients' body.

An ultrasound contrast enhancing agent is any agent which when delivered to the treatment site serves to enhance the visibility of the radioactive source to ultrasound either alone or on reaction with a component of the coating of the source. For example, if the radioactive source is coated with a coating comprising a gas precursor such as $NaHCO_3$, the contrast enhancing agent may comprise an aqueous solution of an acid. Alternatively, if the coating of the radioactive source comprises an acid, the contrast enhancing agent may comprise an aqueous solution of a bicarbonate or carbonate salt. Alternatively, the contrast enhancing agent may be water for injection or saline solution which can react with dry mixtures of bicarbonate or carbonate salts and an acid comprised in the coating of a source.

Alternatively, the contrast enhancing agent may comprise a gas (e.g. perfluorobutane, $N_2$ or $CO_2$) or a gas precursor liquid such as perfluorooctylbromide which can form a gas when heated in the body. Bubbles of gas may thus be produced proximal to a source, so enhancing visibility of the source to ultrasound imaging techniques.

The coating of the invention may also take the form of a capsule or container completely enclosing the carrier and containing air or another gas in the space between the carrier and the coating.

The capsule may comprise a polymer such as those described above as suitable matrix polymers and the gas may be air, fluorocarbon or a gas as described in WO 98/19713. Optionally, the capsule may dissolve after a useful time in the body.

The capsule may be formed by fitting two complementary capsule portions together around the carrier, for example a seed, as in a gelatin capsule, a polymer capsule or a sugar capsule. Alternatively, the capsule can be formed by fitting the carrier into a bag or sack and closing the open end, e.g., by heat sealing, melting, crimping, tying, knotting, twisting, use of adhesive etc.

The polymer shell may become flexible or elastic on treatment with water either prior to or after insertion into a body. Use of low melting plasticizers such as palmitic acid or water-soluble stiffeners such as sugars may optionally be incorporated into the polymer to achieve this.

The coating material for the radioactive sources of the invention may also be wrapped over part of the surface of the carrier. For example, a narrow strip made of Teflon™ or some other suitable biocompatible material with suitable acoustic properties (i.e. materials in which the speed of sound is different to that in water, or with an acoustic impedance different from that of water) may be wound around the outside of a carrier in a helical type fashion in order to introduce transverse surface irregularities. Such irregularities serve to enhance the ultrasound visibility of the source.

Suitable biocompatible polymers include elastomeric polymers which can be wrapped around a source at a temperature above 37° C. and allowed to cool to form a shrink wrapped surface, and which may be fixed to the source with adhesive such as cyanoacrylate or polyvinyl alcohol adhesive or an epoxide adhesive or a hot melt adhesive. Optimally, the elastomer may be formed as a continuous loop and stretched to fit around a source one or more times. Optionally, a helical coating of a polymer may be applied by direct polymerization of polymer or by regional crosslinking of polymer in a helical form. An irregular plastic coating might be fixed in place by glue, by melting or molding, or by designing the coating as a tightly fitting tube with a suitable pattern of wall thickness irregularities such as a helical array of grooves.

Examples of suitable materials include polymers such as polyurethanes, polyethylene, polypropylene, poly(ethylene-co-vinyl acetate) including partially hydrolyzed poly (ethylene-co-vinyl acetate), poly(ethylene-co-vinyl alcohol), polysilicones, polybutylene and isomeric polybutylene such as polyisobutylene, polyisoprene, halogenated rubbers halogenated elastomers such as polyvinyl chloride, polymers and copolymers of vinyl-alkylenes, polymeric ethylene oxides, polyethers, polyacrylates such as poly (hydroxyethyl acrylate), paints such as Chemglaze A276, S13GLO, YB-71, and D-11, which are the paints used on the United States space shuttle, polyepoxides such as polymers of glycidol, polyacrylamides, polypeptides, polyvinylpyrolidone, gelatin and the like.

Optionally, more than one separate source may be contained within the same coating matrix, layer, capsule or container. Optionally, the sources may be separated by a spacer, preferably a radiopaque spacer such as a silver or another metal spacer, or an ultrasound visible spacer such as a gas bubble or a gas-generating substance, such as a diazonium salt, for example benzene diazonium carboxylate.

Preferably, the carrier will further comprise a radiopaque substance, for example silver or another metal, such that the sources may be visualised using X-ray imaging techniques in addition to ultrasound imaging.

Preferred sources of the invention are sealed radioactive sources. Particularly preferred sources are sealed sources comprising a metal container or capsule encapsulating a radioisotope, with or without a support, which can be visualised by both ultrasound and X-ray imaging techniques.

One optional advantage of using the sources of the invention in brachytherapy is that the ultrasound signal and image may be read, measured and analysed by suitable computer software sufficiently quickly to allow a physician to plan real-time dosimetry. This is advantageous from a clinical view point for both patient and medical personnel. However, the sources of the invention may be used in processes involving any type of dosimetry mapping that uses information obtained due to the ultrasound visibility of the sources.

In addition, a physician may use the same imaging technique, i.e. ultrasound, already in place during surgery to confirm both organ (e.g. prostate) position and size, and source placement. This could enable a physician to calculate if additional sources need to be inserted, for example in situations where the dose pattern needs to be recalculated based on the "real" position of the already implanted seeds. Ultrasound imaging provides real time images and is relatively safe for the patient, surgeon and surgical assistants.

Any conventional brachytherapy sources may be coated using the methods of the invention to improve their ultrasound imaging visibility. For example, the ultrasound visibility of the radioactive seeds disclosed in U.S. Pat. No. 5,404,309, U.S. Pat. No. 4,784,116, U.S. Pat. No. 4,702,228, U.S. Pat. No. 3,351,049 and U.S. Pat. No. 4,323,055 (which are incorporated by reference) may be improved by providing a suitable coating.

In a further aspect, the invention provides a coating composition adapted to provide improved ultrasound visibility in vivo for medical or surgical devices and tools that are designed to be implanted or inserted inside a patient's body, including radioactive sources for use in brachytherapy. The coating composition coats the device for at least a part of the time whilst it is in use and provides enhanced detectability by pulse echo ultrasound for at least a part of the time whilst the device is inside a patient's body. Such enhanced ultrasound visibility is useful to aid a physician in placement of the device or tool at the required position inside a patient's body and to monitor the progress of the medical procedure.

Such coated devices themselves form a still further aspect of the invention.

The coating composition comprises essentially non-polymeric biocompatible compounds which in use form a discontinuous coating comprising entrapped bubbles, phase separate regions, entrapped micro domains, or regions of a biocompatible gaseous substance or precursors to a biocompatible gaseous substance, optionally in the presence of a biocompatible membrane forming material as disclosed in U.S. Pat. No. 5,088,499 (column 9), U.S. Pat. No. 5228446 (columns 5 and 6), U.S. Pat. No. 5,123,414 and WO 93/17718, which are incorporated by reference. Other discontinuities can comprise biocompatible metal oxide particles (e.g. $MnO_2$, $Fe_2O_3$) or particles useful as contrast agents in X-ray and MRI imaging, preferably as non-spherical particles. The presence of the discontinuities in the coating improves the ultrasound visibility of coated devices when in vivo.

An advantage of the coating composition of the invention is that if the coating is absorbed by the body through dissolution or metabolism, there will be no harmful side effects for the patient due to the biocompatibility of the coating composition.

The coating composition of the invention preferably comprises a biocompatible material that is in large part not a polymer. The term 'polymer' as used herein is a compound comprising a number of recurring monomer units. Monomer units are compounds of molecular weights less than about 2000. Materials with less than 10 recurring monomer units and preferably less than about 4 recurring monomer units are defined herein as non-polymeric materials. The use of monomeric or dimeric materials is preferred. These materials may be used alone or in mixtures with other monomeric or dimeric materials, the optimum ratios being easily determined by simple trial and error mixing and coating experimentation. Examples of suitable dimeric materials include disaccharides.

Suitable non-polymeric biocompatible compounds for use in the coating compositions of the invention include solids such as sugars, for example sucrose, lactose, fructose, maltose, xylose and the like as described hereinbefore, as well as dimers, trimers, tetramers, etc., up to about decamers of sugar molecules. Other suitable substances include monomeric materials that are solids below about 37° C. such as amino acids, for example naturally occurring amino acids such as aspartic acid and others as described hereinbefore; solid (preferably low melting) iodinated contrast agents such as solid triiodoaromatic compounds, for example iohexol; solid lipid materials, for example stearic acid, palmitic acid and the like, as well as salts, esters and amides of these materials, and dextrins.

Preferably the coating compositions of the invention are in powder form. Such a powder, for example, will desirably be about the consistency of powdered confectioners' icing sugar. Preferably the powders are capable of forming a cake or glaze (i.e. have good cohesive intermolecular forces) if subjected to suitable conditions. Suitable conditions include temporary phase modifying effects such as the application of heat and/or mechanical pressure to cause local melting; the application of a solvent such as water or water vapour or exposure to elevated humidity plus heat and/or mechanical pressure to cause fusion of some or all of the powder to form a coating around the device to be coated. As the coating forms, it should be capable of entrapping biocompatible gas or gases in discrete regions to provide a discontinuous coating.

The coating may comprise more than one layer of fused substance, for example, two or more layers of the same composition coated sequentially, or two or more layers of different compositions coated sequentially. In multi-layer coating, the second or later coatings may comprise in part, for example as isolated or phase separated regions within the coating, a biocompatible polymeric material, for example a polyethylene oxide together with one or more monomeric materials. Such polymeric materials may also comprise phases containing bubbles of gas. The coatings may also comprise silica or polyvinylpyrrolidone or other binding agents.

The coating compositions may also comprise a gas generating substance such as a carbonate or bicarbonate salt, for example a dry mixture of powdered $NaHCO_3$ and an acid such as oxalic, citric, tartaric or aspartic acid. When exposed to suitable conditions, for example to water-containing fluids such as blood or plasma, or by administration or flushing of the source with a water-containing fluid, gas bubbles may be generated proximal to the source. Ultrasound visibility may be improved by the presence of gas bubbles in, on or about the surface of the source. Droplets of perfluorooctyl bromide optionally in a liposome or surfactant bubble (e.g. F108, F68 or albumin) may also be added to the coating compositions.

In a further aspect, the invention provides a method for improving the ultrasound visibility in vivo of medical or surgical devices that are designed to be implanted or inserted inside a patient's body, including radioactive sources for use in brachytherapy, the method comprising providing a composition in powdered form comprising a non-polymeric biocompatible compound, and fusing said composition to form a coating on the device. Preferably, the fusing step is carried out in the presence of a biocompatible gas, for example air or a fluorocarbon, or a liquid that can become a gas on heating, such that bubbles of the gas are trapped in the coating as it forms. Bubbles can form from a gas; from a gas that is subjected to a reduced pressure to cause expansion; from a liquid that is heated to increase its vapor pressure and cause expansion; and from a liquid that is subjected to a reduced pressure to cause a phase change, at least in part, to a gas.

The fusion step may be carried out in a variety of different ways depending on the nature of the coating composition and the device to be coated. Possible coating methods include conventional coating techniques, blow coating, fusion coating, hot melt coating, dipping the device into heated (molten) coating material, rolling a heated device in powder, sputter coating, spray coating, and applying mechanical pressure (and optionally heat) to compact the powder. Mechanical compaction is a preferred method. A gas may be present at elevated pressure or reduced temperature prior to applying mechanical pressure or heat to the powdered coating, such that bubbles of the gas are trapped in the coating as it forms.

For example, the device to be coated may be heated and then introduced into an excess of the powdered coating composition such that the composition melts and forms a coating around the device as it cools. The thickness of the coating will depend in part on the melting point of the coating composition, and on the temperature and heat capacity of the device to be coated. Preferably, this process is carried out in the presence of a gas, for example a fluorocarbon, in particular a fluorocarbon under a pressure greater than one atmosphere, for example at a pressure of about 1.1 to about 10 atmospheres or more.

Alternatively, the device to be coated may be covered with the powdered composition and then the composition heated to cause fusion to form a coating. Heating to melt the powder coating may be by means such as heated air, convection heating, microwave heating, infrared heating, resistance heating, conductance heating, and the like. On cooling, the coating will substantially harden around the device.

Optionally, prior to coating, the device may first be wetted with a suitable solvent depending on the nature of the coating composition, for example with water, with ethanol and water or with one or more other suitable solvent combinations. The wetting may create a transient layer of solubilized powder composition that may serve as an adhesive, cohesive or tackifing layer to promote the adhesion of additional coating composition.

The coating and fusing steps may be repeated as required to produce a coating comprising two or more layers. During repeated coating steps, the outermost coating layer may optionally be treated one or more times at one or more locations with an etching step to create pits, bubbles or pores which may contain gas or gas precursor and which may then be over-coated with additional layer(s) of fused powder coating. Suitable etching methods include abrasion, solvent etching, and selective dissolution of part of the coating, for example dissolution of a salt from a hydrophobic or more high energy sugar coating in water. Preferably, etching of the outermost coating layer may be done after each layer is applied, up to and even including the final layer.

Optionally, a gas generating substance may be added to the powder during one or more of the coating steps.

Optionally, the surface of the device to be coated is roughened prior to the coating step. This surface roughness may also serve to enhance the ultrasound visibility of the coated devices. In addition, a roughened exterior surface may serve to trap additional amounts of gas during the coating step.

In all the methods of the invention, the coating should be thick enough such that the ultrasound visibility of the device or tool is enhanced, but not so thick that the coating interferes with the normal use of the device or tool.

In a further aspect, the invention provides a further method for enhancing the ultrasound visibility in vivo of medical or surgical devices or tools that are designed to be implanted or inserted inside a patient's body, including radioactive sources for use in brachytherapy, the method comprising delivering a contrast agent to the site of implantation or insertion. Preferred contrast agents comprise a gas. The contrast agent may be delivered directly to the site of implantation or insertion or a precursor may be delivered to the site and the contrast agent generated in situ.

Suitable means include providing salts and/or solutions that are capable of generating gas at the site of the implanted or inserted device. Suitable gas producing precursors include salts which may generate carbon dioxide or another biocompatible gas in situ, for example when exposed to acidic or aqueous conditions. Such salts include carbonate or bicarbonate salts (e.g. sodium, potassium, iron, calcium, meglumine or polymer-bound ammonium salts), optionally together with a nascent acid source. Other gas generating combinations may also be useful. These include peroxides and metal ions. Useful peroxides include hydrogen peroxide, carboxylic acid peroxides such as alkyl peracids, peracids of sulfur (persulfates), of boron (perborates), or of phosphorus (perphosphates) and the like, as well as polymer bound peracids. Useful metal ions include ferrous and ferric ions. Optionally, metals such as platinum and palladium that can catalytically convert peroxides to oxygen gas can be used.

One component or both components of a gas generating system may be provided as a solid in pellet form or as a coating for a device. Alternatively, one component (e.g. solid $NaHCO_3$) of a gas generating system may be included in a pellet or a coating and the other component (e.g. citric acid or acetic acid) added as an irrigating solution (e.g. in water), for example via a needle, once the pellet or device is in place, to generate gas bubbles.

The pellets or coating may optionally comprise a binder. A binder is a material that adds cohesive strength to the pellet or coating. Examples of suitable binders include gelatin, polyvinylpyrrolidone (PVP), silica, polyvinyl alcohol, dextrin, cyclodextrin, gum, starch, albumin, and poly(ethylene-co-vinyl acetate). The pellets may be inserted or implanted proximal to the device, preferably at the time of implantation or insertion of the device but optionally before or afterwards, or may be attached to it, for example using a biocompatible glue such as a silicone adhesive, a cyanoacrylate or epoxy adhesive, or a urethane adhesive. Preferably, the pellet is of a similar cross-sectional dimension as the device. If the device is a radioactive source for use in brachytherapy, the pellet may be of a similar overall size and shape to the source itself. The source may then be readily implanted or inserted using the same methodology as for the implantation or insertion of the brachytherapy source itself. For example, a pellet may be placed in a syringe needle in front of and/or behind a brachytherapy source such as a seed and implanted next to the source.

Optionally, a pellet and a brachytherapy source may be entrained in a polymer matrix such as a urethane, poly (ethylene-co-vinyl acetate) or silicone matrix. Preferably, a component of the matrix is permeable to water or will dissolve in water. Optionally, a seed may be inserted into a pellet volume after the pellet has been hydrated.

Suitable acid sources for use in the method of the invention include carboxylic acids, phosphorous acids such as phosphoric acids, sulfonic acids, and the like. Examples of carboxylic acids include hydroxyl-substituted carboxylic acids, citric acid, ascorbic acid, amino acids such as aspartic acid and glutamic acid, dicarboxylic acids such as succinic acid, alkyl acids such as stearic acid, polymeric acids such as acrylic acid and polyaspartic acid.

The acid may be a solid and dry formulated with a gas precursor salt, optionally with a binder such as PEG or PVP, and optionally with a surface active agent such as a surfactant (e.g. PEG stearate, Pluronic surfactant, F68, F108, ascorbyl palmitate), a protein (e.g. albumin), a sugar (e.g. lactose, sucrose) or a release agent (e.g. sodium stearate). The release agent or surfactant may optionally be present on the exterior of the pellet. Iohexol or a surfactant comprising iohexol (such as a methoxy PEG adipate ester of iohexol) may also be used in the pellets.

Optionally, the pellet may contain hydratable materials such as sugars, amino acids or citric acid. Hydration of the pellet may be achieved by permitting or facilitating contact with water-containing fluids such as blood or by administration or flushing of the pellet with a water-containing fluid (e.g. water for injection, phosphate buffered saline) for example via a syringe either at the time of implantation or afterwards. Hydration of the pellet may generate ionized $H^+$ (or $H_3O^+$) which in the presence of, for example, hydrated $HCO_3^-$, will generate $CO_2$ gas.

The gas will form one or more bubbles and reside proximal to the device. The gas and hence the device will be more visible when viewed using ultrasound imaging devices used commonly for in vivo diagnostic imaging.

Alternatively, a solution of one component (e.g. of sodium bicarbonate) can be added via a needle to the vicinity of an implanted or inserted device, followed by delivery of a solution of another component (e.g. of an acid) via the same or a different needle. The two components may then react together to generate a gas in situ. Optionally, one or both solutions may comprise a surfactant, or a surfactant may be added as a separate solution, optionally prior to addition of the components.

In another aspect of the invention, a gas (e.g. perfluorobutane, $N_2$ or $CO_2$) or a gas precursor liquid such as perfluorooctylbromide which can form a gas when heated in the body may be added, for example via a syringe, to the vicinity of an implanted or inserted device. Bubbles of gas may thus be produced proximal to the device and the device will be more visible by ultrasound imaging techniques.

Optionally a proximal surfactant or excipient may also be introduced to aid gas bubble formation. Useful excipients include PEG and PEG esters of carboxylic acids, surface active agents, albumin, alpha tocopherol, ascorbic acid, ascorbyl palmitate, calcium stearate, cetyl alcohol, esters of cetyl alcohol, cholesterol, citric acid, indocyanine green, polyvinylpyrrolidone, dextrin, cyclodextrin, dextrose, ethyl oleate, fructose, gelatin, glycerin and glycerin esters, lactic acid, lactose, mannitol, meglumine, mineral oil, corn oil, poloxamers, sorbitan esters, sodium ascorbate, stearyl alcohol, sucrose, tartaric acid, iohexol, iodinated contrast agents, MRI contrast agents, ultrasound contrast agents such as Albunex, Levovist, Acuson, NC100100 (see WO97/29783), lipid based ultrasound agents, especially fluorocarbon-containing ultrasound agents, and emulsifying agents such as phosphatidyl serine and the like.

Optionally, the method may be used in combination with a device which comprises a roughened surface or includes a roughened surface segment. Gas produced proximal to the surface of the device can reside for a longer period at or near the roughened surface. This can result in enhanced visibility of such a device due to both the ultrasound reflecting properties of the roughened surface and to the presence of gas bubbles residing adjacent to or on the surface of the device.

In a further aspect, the invention provides a further method for improving the ultrasound visibility in vivo of medical or surgical devices or tools that are designed to be implanted or inserted inside a patient's body, including radioactive sources for use in brachytherapy, the method comprising providing a coating comprising a liquid or polymer which alters its ultrasound imaging properties upon elevating the temperature from ambient (about 25° C.) to physiological (about 37° C.) temperature or on a change of pH. Such polymers include polymers which chemically emit a gas from their covalent structure upon temperature elevation or a change in pH. Examples of such polymers include those which contain alpha-carboxy glycine groups which de-carboxylate at neutral pH to generate $CO_2$ gas. Alternative polymers and coatings which similarly decompose in vivo to emit a gas, include for example polymers containing beta-keto acids or malonic acids which can decarboxylate on acidification and/or heating, or polymers containing vicinal dicarboxylic acid copper salts which can decarboxylate on heating.

Further examples of such coatings include coatings comprising a fluid which evaporates between ambient (about 25° C.) and physiological (about 37° C.) temperature. Such liquids (e.g. perfluoroalkanes and cycloperfluoroalkanes) are disclosed in WO 92/17212, WO 92/17213, WO 93/00930, WO 94/21301 and WO 94/06477, which are incorporated by reference. These liquids may, for example, be encapsulated within polymers to seal them in or they may be applied onto the surface of a device, for example in the form of gels, creams or sols which could then optionally slough off during entry into a patient's body. If the device is a radioactive source for use in brachytherapy, then the source and optionally the applicator needle could both be rendered more visible to ultrasound.

Suitable-coating or application methods are known in the art. They include dipping or rolling the device in a solution, mixture or melt of the coating material, spray coating, brush coating or painting. A device may also be coated with a suitable pre-polymer which is then polymerised in situ, for example by exposure to water or light. WO98/19713 discloses suitable coating methods.

In a further aspect, the invention provides a method for improving the ultrasound visibility in vivo of medical or surgical devices or tools that are designed to be implanted or inserted inside a patient's body, including radioactive sources for use in brachtherapy, the method comprising coating part of a surface of the device with a thin layer of magnesium.

Such magnesium-coated devices themselves form a still further aspect of the invention.

When such a coated device comes into contact with water, the magnesium starts to react and produces small bubbles of hydrogen gas. Gas bubbles are very compressible and hence highly visible in an ultrasound image. Magnesium ions are not known to be toxic.

The method used to coat the devices of the invention will depend in part on the nature of the device to be coated. For example, plastic devices may be coated by sputtering and by vapour deposition, whilst metal devices may be coated by vapour deposition, by dipping in molten magnesium, by sputtering or by electroplating in a non-aqueous solvent such as acetonitrile with a solution of e.g. $Mg^{2+}$. It is necessary to use water-free conditions since magnesium reacts with water, although the reaction can be quite slow.

The product formed from the reaction of e.g. 24 $\mu$g of magnesium metal in vivo will be a very small amount of hydrogen, 25 $\mu$l (~1 $\mu$mol), and magnesium hydroxide (58 $\mu$g, 1 $\mu$mol). These amounts are estimated to be so small that they will have little or no effect on the organism.

Vapor deposition may be performed according to the following procedure: the device (metal or plastic) is cleaned of non-adhering substances including grease, oil and surfactants, with an organic solvent such as methylene chloride for metals and heptane or ether or other solvent, which will not dissolve or alter the shape of the plastic material for plastics, dried and placed in a vessel together with a small amount of magnesium metal. A mixture of soap or detergent in water or water and alcohol followed by a rinse with water or water and alcohol may also be used. The vessel is evacuated and filled with argon or nitrogen at least three times. The vessel is revacuated to <1 mbar and the part of the vessel proximal to the magnesium is heated to just above the melting point of magnesium (651° C.) for a few seconds. A thin film of magnesium will be deposited on the device located in the space above the metal. Argon is let into the system and after cooling the device is taken out and can be handled in normal indoor conditions. When a radioactive source such as a seed is coated by this method, the entire surface may be coated with magnesium or only a part of the surface may be coated. Optionally, the coating thickness may be uniform or it may be non-uniform on the coated surface.

Electroplating of metal devices may be performed according to the following procedure: the device to be covered is cleaned and dried and connected to the negative pole, and a magnesium electrode is connected to the positive pole, of a DC current supply. An inert solvent such as acetonitrile and a supporting electrolyte is added. A suitable voltage is applied and the electrolyte is stirred until a desired thickness of magnesium has been deposited on the device to be coated.

The thickness of the magnesium metal layer will determine how long the gas generating effect lasts, but typically this will be a few hours. The thickness of the coating layer should be such that the ultrasound visibility of the device is enhanced but not so thick that the device cannot be used as normal.

Suitable devices for coating include brachytherapy sources including seeds, biopsy and puncture needles, catheters, syringe needles, tubing, clamps, drainages, and surgical instruments and implants.

The invention will be further illustrated, by way of example, with reference to the following Drawings.

Figure 4A:
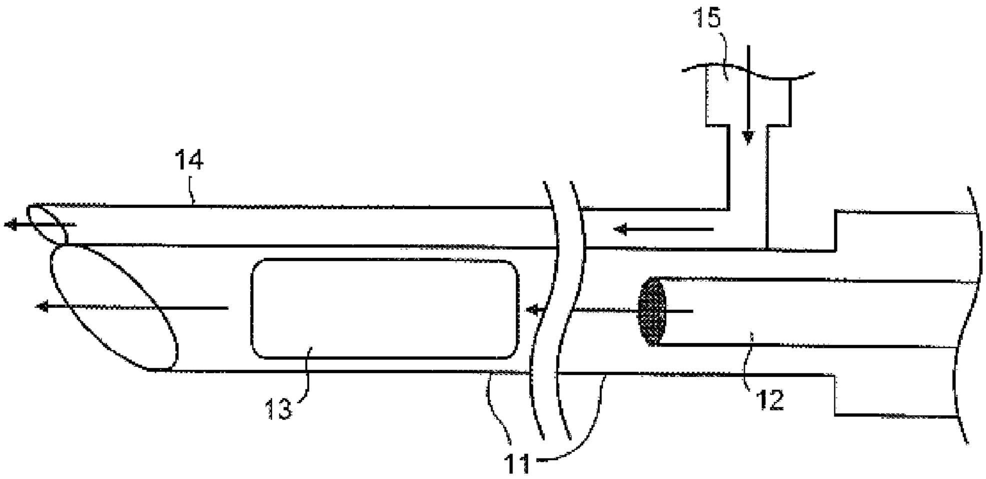
Figure 4B:
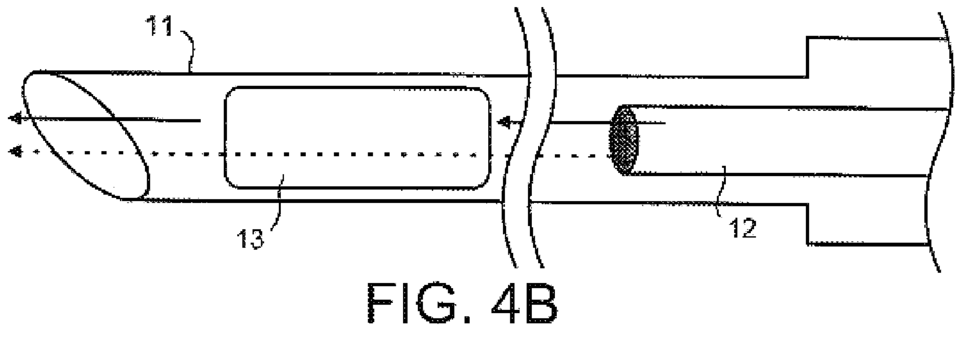

FIGS. 3A–D are ultrasound images which are discussed in more detail in the following Examples;

FIGS. 4A and 4B illustrate delivery devices suitable for delivery of a radioactive source and an ultrasound contrast enhancing agent to a site to be treated within a patient.

Figure 1:
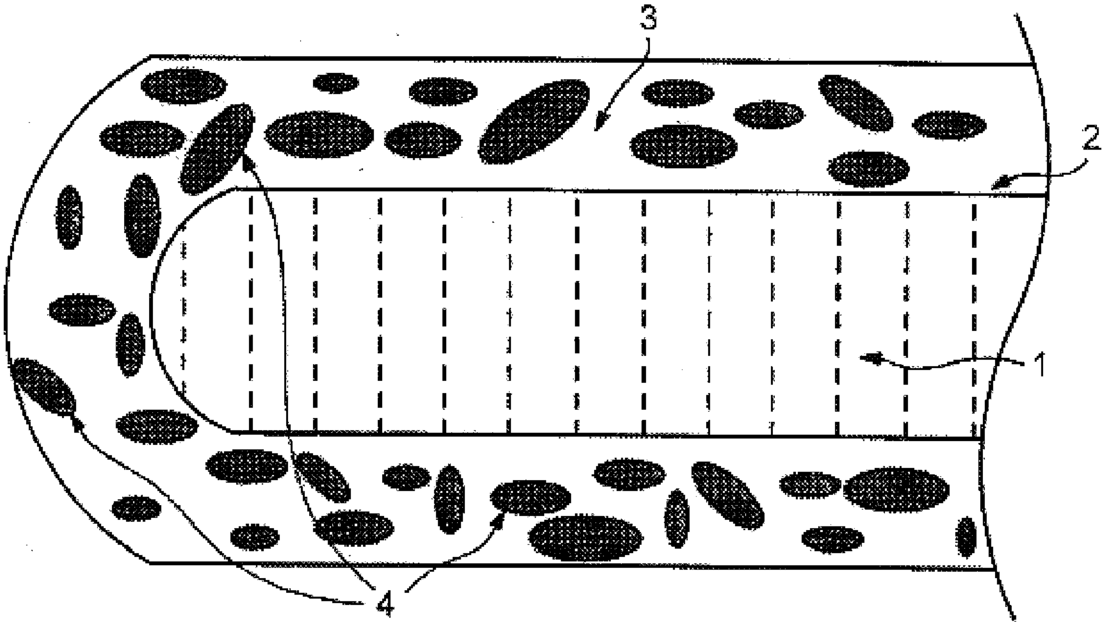
FIG. 1 illustrates one embodiment of a radioactive source according to the invention.

FIG. 1 illustrates in schematic form a radioactive source 1 according to the invention comprising a carrier and a radioisotope encapsulated in a metal container 2, for example a titanium or stainless steel seed. The outside of the container 2 is coated with a matrix material 3 containing domains of encapsulated bubbles or particles 4.

Figure 2:
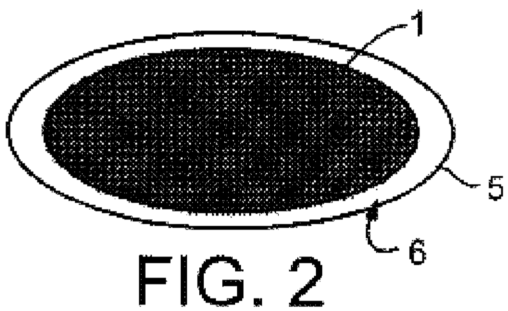
FIG. 2 illustrates another embodiment of a radioactive source according to the invention.

FIG. 2 illustrates in schematic form another embodiment of a radioactive source according to the invention. The source 1 is contained inside a capsule 5 and a layer of gas 6, for example air, is trapped between the capsule 5 and the source 1.

FIGS. 4A and 4B illustrate in schematic form two delivery devices suitable for delivery of a contrast enhancing agent to the site of insertion or implantation of a radioactive source. The needle 11 and plunger 12 can be formed of an inert biocompatible material such as stainless steel, ceramic, glass or plastic, and should be sterilisable. The bore of the source delivery needle 11 should be large enough for a radioactive source 13 to pass. The pointed end of the needle can be tapered or blunt.

The devices also comprise a tube 14 for delivery of an ultrasound contrast enhancing agent. The bore of the tube 14 should be large enough to permit delivery of a diagnostically useful amount of contrast agent or a liquid to the vicinity of the source. The volumes can be found empirically but are estimated to be within the range of from 1/100 of a microliter to about 10 ml. In FIG. 4A, the delivery tube 14 is on the outside of the needle 11 and is substantially parallel with it. In FIG. 4B, the tube 14 is part of the plunger 12.

The contrast enhancing agent delivery tube 14 may be connectable to a reservoir 15 of the agent, such as a syringe or canister, and optionally comprises an on-off valve (not shown). A suitable connector comprises a swagelock fitting on the delivery tube. Optionally, the exterior of the needle may be calibrated in linear dimensions (ruled) such as centimeter, millimeters, inches, fractions of inches, etc. to aid the surgeon during implantation procedures.

The invention will be further illustrated with reference to the following non-limiting Examples:

EXAMPLES

Example 1

Magnesium-coated Titanium Wire

A length of titanium wire (mm) was cut into two roughly equal pieces. Both pieces were cleaned with acetone and wiped dry. One piece was kept as a control and the other was coated with a thin layer of magnesium by vapor deposition. The wire to be coated was placed in a pressure vessel with a small amount of magnesium metal. The vessel was evacuated to <1 mbar and heated to just above 651° C. for a few seconds. Argon was then let into the system and the coated wire allowed to cool to ambient temperature. Both wires were stored under Argon.

Ultrasound Imaging

The control wire was inserted into a 1 kg steak and two ultrasound images were recorded, one section through the long axis of the wire and one cross-section. The control wire was then removed and the magnesium coated wire inserted into the steak in the same position. Two ultrasound images were taken, corresponding to those taken of the control wire. FIGS. 3A to D show the resulting ultrasound images. The ultrasound machine used was an ACUSON XP10 (Acuson, Mountainview, Calif., USA). Transducer: 5 MHz linear array.

Figure 3A:
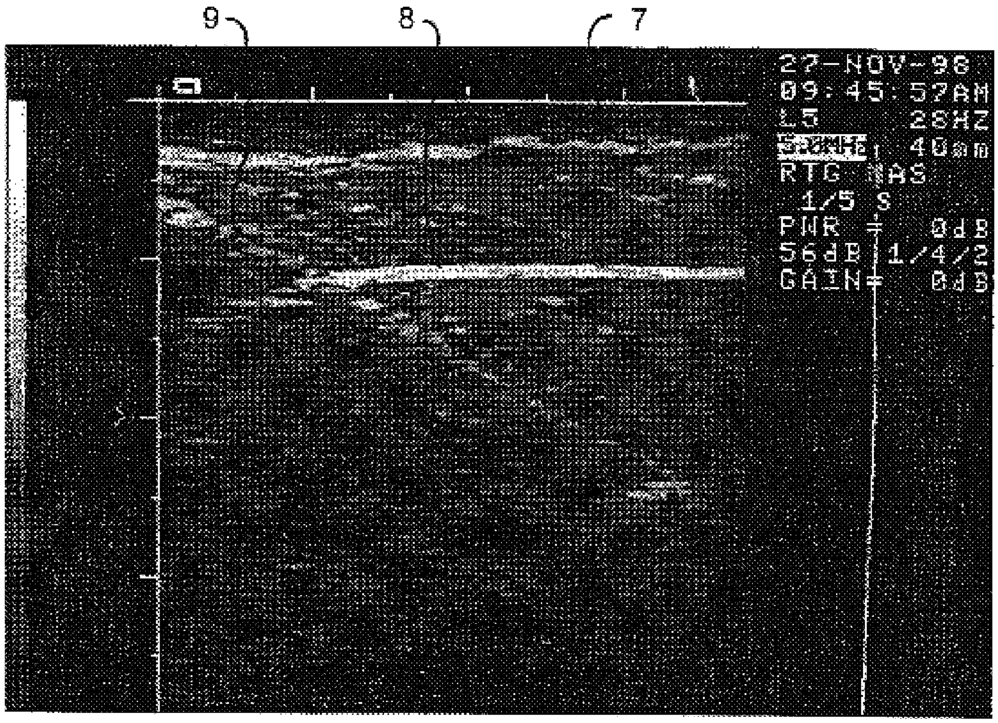

FIG. 3A is the longitudinal view of the control wire.

Figure 3B:
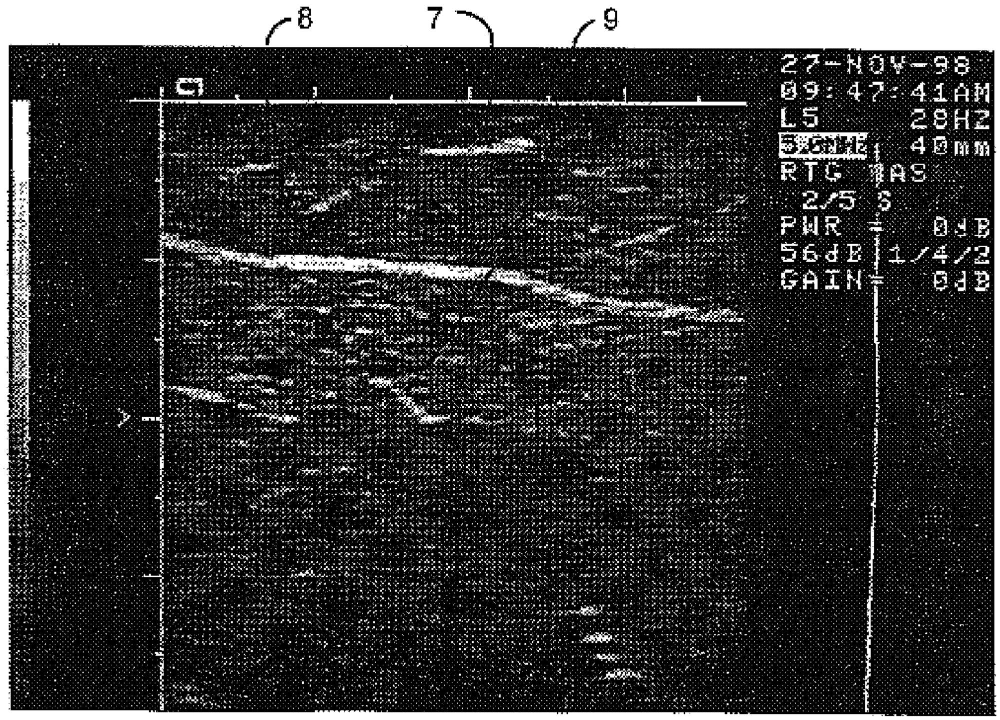

FIG. 3B is the cross-sectional view of the control wire.

Figure 3C:
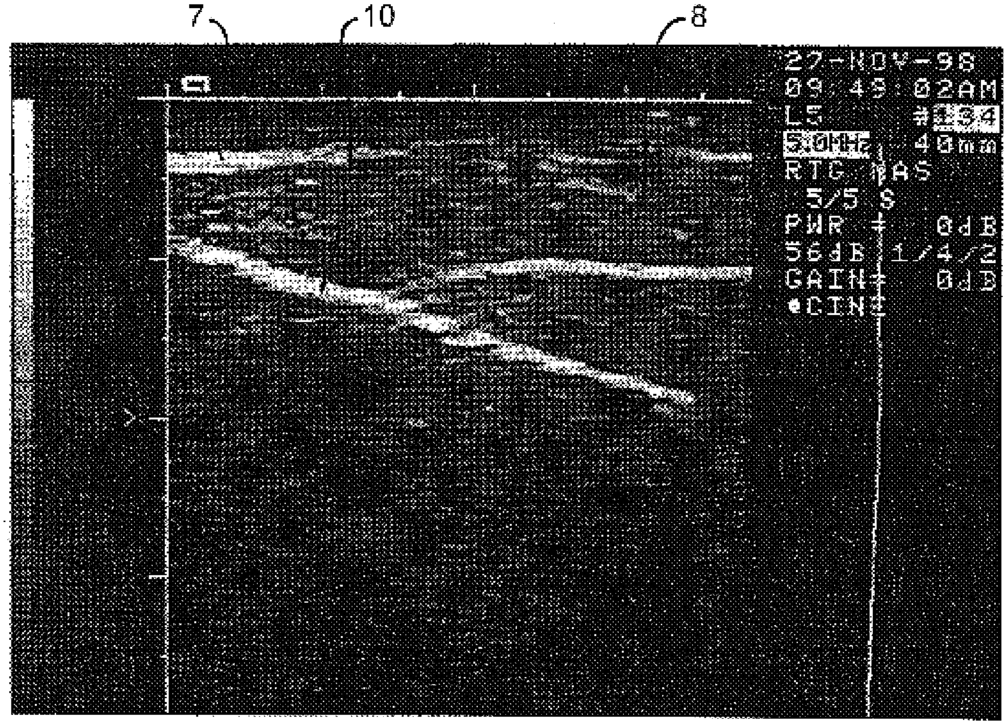

FIG. 3C is the longitudinal view of the magnesium coated wire; and

Figure 3D:
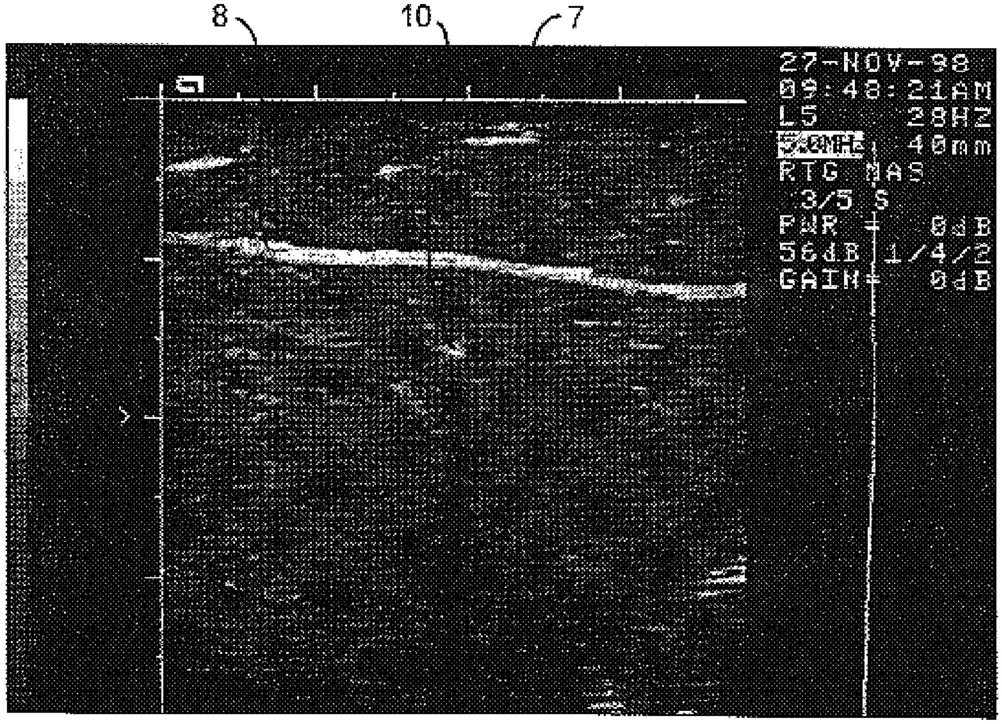

FIG. 3D is the cross-sectional view of the magnesium coated wire.

In FIGS. 3A to D, 7 indicates the surface of the meat and 8 indicates a structure within the meat. In FIGS. 3A and 3B, 9 indicates the control wire, whilst in FIGS. 3C and 3D, 10 indicates the coated wire.

A comparison of FIGS. 3A and 3B with 3C and 3D clearly shows the improved ultrasound visibility of the magnesium-coated wire compared to the control wire.

Example 2

Magnesium-coated Titanium Seed Containing a Radioisotope

The surface of a No. 6711 I-125 seed (available from Nycomed Amersham) is cleaned with distilled water, then washed with acetone and dried. The seed is placed in a cavity 0.9 mm wide and 2.25 mm deep that is drilled radially in the middle of a 6.3 mm diameter by ~30 cm long graphite rod (Johnson Matthey Co., Inc.). The rod is suspended horizontally at each end between two glass wool plugs inside a ~2 cm inner diameter quartz tube. The tube also contains a localized layer comprising approximately 10 mg of 50 mesh magnesium granules (vacuum deposition grade, Aldrich) spread at the midpoint of the tube such that the seed is located and held horizontally over the magnesium with the seed positioned near the center of the tube diameter. The tube is also configured with ground glass joints at each end to which are attached a vacuum reduction adapter and an argon inlet adapter configured with a vacuum stopcock. The tube is positioned in a tube furnace (VWR Scientific), and the volume of the tube is flushed for several minutes with argon. The tube is then evacuated to <1 mbar, and the region of the tube proximal to the magnesium is heated to just above the melting point of magnesium (about 700° C.) for a few seconds. A thin film of magnesium is deposited on the exposed portion of the seed. The tube is cooled, argon is reintroduced, and the graphite rod with seed is withdrawn. The seed is then inverted into the graphite such that the magnesium-coated end of the seed is placed in the cavity. The vapor deposition process is then repeated in a second coating step to provide a seed having a continuous coating of magnesium metal. If desired, a partial coating of magnesium can be obtained by eliminating the above second coating step. A coating on more or less than half the seed can be obtained by using a cavity of appropriate depth: the portion of the seed above the cavity will be coated. The coated seed is stored under argon until used.

Ultrasound Imaging

A control No. 6711 I-125 seed is inserted into a one kilogram steak and two ultrasound images are recorded using an Acuson XP10 machine equipped with a 5 MHz transducer that is acoustically coupled to the surface of the steak. The orientation of the transducer for one image is parallel to the long axis of the seed; the orientation of the transducer for the other image is perpendicular to the long axis of the seed. The control seed is then removed and a magnesium-coated No. 6711 I-125 seed prepared according to the above procedure is inserted into the steak in the same position. Two ultrasound images are taken with the orientations of the images corresponding to those of the control seed. The seed coated with magnesium is more visible than the control seed in the respective orientations.

Example 3

Priming the Surface of a Titanium Seed With an Acrylic Acid

The surface of a No. 6711 I-125 seed (available from Nycomed Amersham) is cleaned with acetone and dried. The seed is then immersed in a 0.5 N aqueous sodium hydroxide solution containing 10% by volume of 30% hydrogen peroxide for about 10 minutes. The seed is then washed with hot water for about ten minutes, and dried with warm dry air. One end of the seed is clamped in a compression chuck mounted horizontally on the end of a drive shaft of a variable speed motor. The seed is rotated along its axis at about 100 rpm while a one per cent solution of a mixture of poly (ethylene-co-acrylic acid) and poly(tolylene 2,4-diisocyanate) dissolved in butyl acetate, cyclohexanone and tetrahydrofuran is applied as a spray to the exposed portion of the seed. The solvent is allowed to evaporate in a stream of warm air and the coating is cured in air. The seed is then inverted in the chuck, the spray coating is repeated on the exposed uncoated surface, and the coating is dried.

Example 4

Priming the Surface of a Titanium Seed With a Polyurethane Primer

The method of example 3 is repeated followed by a spray application of a polyurethane primer dissolved in mineral spirits. The solvent is evaporated in air.

Example 5

Priming the Surface of a Titanium Seed With a Sol Gel

A clean No. 6711 I-125 seed is immersed in an aqueous sodium hydroxide solution containing hydrogen peroxide, rinsed with hot water, immersed in nitric acid, then rinsed with water. The seed is then immersed for about quarter of an hour in an active 4% sol gel reaction mixture. The sol gel is prepared by adding 3 parts glacial acetic acid, 1 part tetrapropyl zirconate (70% in 1-propanol) and parts of water to 4 parts of 3-glycidoxypropyltrimethoxysilane and 50 parts of water one half hour after mixing the latter, diluting to 4% with water, and aging for several hours. The seed is removed from the reaction mixture, drained and dried at room temperature for about an hour, and then dehydrated at 110° C. for about minutes.

Example 6

Overcoating the Surface of a Titanium Seed With a Sol Gel and a Polyurethane Primer The sol gel coated seed of example 5 is treated with a spray application of a polyurethane primer dissolved in mineral spirits. The solvent is evaporated in air.

Example 7

A seed prepared by the method of example 3 is dip-coated with a mixture of 20 parts of toluene diisocyanate and Desmodur IL, 40 parts tetrahydrofuran and 40 parts dimethyl sulfoxide at ambient temperature. The ratio of toluene diisocyanate to the Desmodur can range from 19:1 to about 1:19. Excess coating solution can be removed from the seed using a surface tension wick tip. The solvent is partially evaporated and the seed is immersed in water for about two minutes to initiate hydrolysis of some of the isocyanate functional groups. Bubbles of carbon dioxide are formed and are trapped in the polymer coating. The seed is removed from the water, heated and dried in warm air prior to examination by ultrasound medical imaging techniques. The coated seed is more visible to detection by ultrasound imaging than an uncoated No. 6711 I-125 seed.

Example 8

A seed prepared by the method of example 4 is dip-coated with a mixture of 20 parts of toluene diisocyanate and Desmodur IL, 40 parts tetrahydrofuran and 40 parts dimethyl sulfoxide at ambient temperature. The ratio of toluene diisocyanate to the Desmodur can range from 19:1 to about 1:19. The solvent is partially evaporated and the seed is immersed in water for about two minutes to initiate hydrolysis of some of the isocyanate functional groups. Bubbles of carbon dioxide are formed and are trapped in the polymer coating. The seed is removed from the water, heated and dried in warm air prior to examination by ultrasound medical imaging techniques. The coated seed is more visible to detection by ultrasound imaging than an uncoated No. 6711 I-125 seed.

Example 9

A seed prepared by the method of example 5 is dip-coated with a mixture of 20 parts toluene diisocyanate and Desmodur IL, 40 parts tetrahydrofuran and 40 parts dimethyl sulfoxide at ambient temperature. The ratio of toluene diisocyanate to the Desmodur can range from 19:1 to about 1:19. The solvent is partially evaporated and the seed is immersed in water for about two minutes to initiate hydrolysis of some of the isocyanate functional groups. Bubbles of carbon dioxide are formed and are trapped in the polymer coating. The seed is removed from the water, heated and dried in warm air prior to examination by ultrasound medical imaging techniques. The coated seed is more visible to detection by ultrasound imaging than an uncoated No. 6711 I-125 seed.

Example 10

A seed prepared by the method of example 6 is dip-coated with a mixture of 20 parts toluene diisocyanate and Desmodur IL, 40 parts tetrahydrofuran and 40 parts dimethyl sulfoxide at ambient temperature. The ratio of toluene diisocyanate to the Desmodur can range from 19:1 to about 1:19. The solvent is partially evaporated and the seed is immersed in water for about two minutes to initiate hydrolysis of some of the isocyanate functional groups. Bubbles of carbon dioxide are formed and are trapped in the polymer coating. The seed is removed from the water, heated and dried in warm air prior to examination by ultrasound medical imaging techniques. The coated seed is more visible to detection by ultrasound imaging than an uncoated No. 6711 I-125 seed.

Example 11

The method of example 7 is repeated using a mixture of toluene diisocyanate and Desmodur N-100.

Example 12

The method of example 8 is repeated using a mixture of toluene diisocyanate and Desmodur N-100.

Example 13

The method of example 9 is repeated using a mixture of toluene diisocyanate and Desmodur N-100.

Example 14

The method of example 10 is repeated using a mixture of toluene diisocyanate and Desmodur N-100.

Example 15

The method of example 7 is repeated using a mixture of toluene diisocyanate and Desmodur N-3200.

Example 16

The method of example 8 is repeated using a mixture of toluene diisocyanate and Desmodur N-3200.

Example 17

The method of example 9 is repeated using a mixture of toluene diisocyanate and Desmodur N-3200.

Example 18

The method of example 10 is repeated using a mixture of toluene diisocyanate and Desmodur N-3200.

Example 19

The method of example 7 is repeated using a mixture of toluene diisocyanate and Desmodur Z4370.

Example 20

The method of example 8 is repeated using a mixture of toluene diisocyanate and Desmodur Z4370.

Example 21

The method of example 9 is repeated using a mixture of toluene diisocyanate and Desmodur Z4370.

Example 22

The method of example 10 is repeated using a mixture of toluene diisocyanate and Desmodur Z4370.

Example 23

The method of example 7 is repeated using a mixture of toluene diisocyanate and Desmodur MP-100.

Example 24

The method of example 8 is repeated using a mixture of toluene diisocyanate and Desmodur MP-100.

Example 25

The method of example 9 is repeated using a mixture of toluene diisocyanate and Desmodur MP-100.

Example 26

The method of example 10 is repeated using a mixture of toluene diisocyanate and Desmodur MP-100.

Example 27

The methods of examples 7 to 26 are repeated using a drop coating technique wherein a drop of isocyanate-containing coating material is applied to the top end of a seed held vertically upward in a rotating chuck. The coating material is spread downward by the force of gravity and uniformly by the rotating motion of the spinning seed in the chuck to cover the portion of the seed exposed from the chuck.

Example 28

Coating the Surface of a Titanium Seed With Metal Particles in a Matrix

The surface of a No. 6711 titanium seed was cleaned with acetone and dried. The seed was then immersed for one minute in a solution, heated to 55° C., comprising 5 parts of poly(ethylene-co-acrylic acid) [containing 15% acrylic acid, Aldrich], 50 parts of toluene, and 45 parts of cyclohexanone. The seed was removed from the polymer solution, placed in a horizontal compression chuck mounted on the end of the drive shaft of a variable speed motor, rotated at 100 rpm, and heated with hot air for about seconds. After cooling to ambient temperature, the accessible end of the rotating seed was brush-coated using a tapered cotton wick applicator with a suspension comprising 21% bronze metal particles in a vehicle of styrene resin dissolved in xylol. The solvent was allowed to evaporate in a stream of warm air. Coatings of other particles can be formed in a similar fashion.

Example 29

A No. 6711 titanium seed was coated with poly(ethylene-co-acrylic acid) and placed in a rotating horizontal compression chuck according to the method of Example 28. The accessible end of the rotating seed was brush-coated with a pattern comprising two parallel stripes spaced approximately 1 mm apart. The pattern was applied using a linear 0.18 mm thick wick applicator and a suspension comprising 21% bronze metal particles in a vehicle of styrene resin dissolved in xylol. The seed was then over-coated with a second stripe pattern spiraling down the length of the seed. The striped pattern was formed by slowly moving the applicator along the length of the rotating seed. The solvent was allowed to evaporate in a stream of warm air. Coatings of other patterns and of other particles can be formed in a similar fashion.

Example 30

A No. 6711 titanium seed was coated with poly(ethylene-co-acrylic acid) and placed in a rotating horizontal compression chuck according to the method of Example 28. The accessible end of the rotating seed was brush-coated with a stripe pattern that wound spirally along the seed with stripes spaced approximately 0.5 mm apart. The pattern was formed using a linear cotton thread wick applicator and a suspension comprising 21% bronze metal particles in a vehicle of styrene resin dissolved in xylol. The solvent was allowed to evaporate in a stream of warm air. Coatings of other patterns and of other particles can be formed in a similar fashion.

Example 31

Microbubble Coated Titanium Tubes

Titanium tubes identified as "before polishing" were used as model substrates for the coating. These tubes were dimensionally the same (diameter and approximate length) as the finished seed product but had not been polished in a subsequent milling operation. Hence, the surface of these tubes was rougher than the normal seed container. These tubes were attached at the center to the end of a small diameter (<0.8 mm) drill bit with a drop of cyanoacrylate adhesive (i.e., Superglue). The attached tubes were then submerged in a solution of microbubbles (as described in WO 97/29783) containing approximately 0.2% hydroxymethylpropyl cellulose and 3% Pluronic F-108 surfactant. The solution was allowed to dry on the tube at room temperature.

These tubes were then compared with conventional polished tubes for echogenicity in an in vitro phantom device. The polished tubes were more echogenic than uncoated unpolished tubes. This "phantom" was prepared from a conventional prostate phantom used for training in the insertion of seeds (obtainable from Computerised Imaging Reference Systems, Inc, of Norfolk, Va., U.S.A.) and had a compartment that accepted the transrectal ultrasound probe used as a guide during the procedure. The box was rotated onto its side such that the transrectal probe was now beside the test compartment rather than below. The new top of the box was removed for accessibility and the phantom anatomy removed. The gel lined compartment was then used as a water bath for comparison of different seeds and tubes echogenicity.

Qualitative tests showed that the coated tubes were at least as echogenic as traditional tubes and retained that activity over a wider range of angles relative to the probe than did the polished tubes. In addition, using color doppler ultrasound mode, the presence of active microbubbles on the tube was determined by the flashing colours of bubbles breaking under the influence of the ultrasound energy. This energy could be lessened such that the bubbles didn't rupture whilst providing a very good image of the tubes themselves.

Example 32

Microbubble Coated Seeds

The titanium seeds for use in this Example are dummy seeds which do not contain any radioisotopes and so are non-radioactive.

Titanium seeds identified as "before polishing" are used as substrates for the coating. These seeds are dimensionally the same as the finished product but have not been polished in a subsequent milling operation. Hence, the surface of these seeds is rougher than the normal seed container. These seeds are attached at the center to the end of a small diameter (<0.8 mm) drill bit with a drop of cyanoacrylate adhesive (i.e., Superglue). The attached seeds are then submerged in a solution of microbubbles (as described in WO 97/29783) containing approximately 0.2% hydroxymethylpropyl cellulose and 3% Pluronic F-108 surfactant. The solution is allowed to dry on the seed at room temperature.

These seeds are then compared with conventional seeds for echogenicity using an in vitro device. This "phantom" is prepared from a conventional prostate phantom used for training in the insertion of seeds (obtainable from Computerised Imaging Reference Systems, Inc, of Norfolk, Va., U.S.A.) and which has a compartment that accepts the transrectal ultrasound probe. This is used as a guide during the procedure. To be an acceptable in vitro phantom, the box is rotated onto its side such that the transrectal probe is now beside the test compartment rather than below. The new top of the box is removed for accessibility and the phantom anatomy removed. The gel lined compartment is then used as a water bath for comparison of different seeds and seeds for echogenicity.

Coated seeds are as echogenic as traditional seeds and may retain that activity over a wider range of angles relative to the probe than the traditional seeds. In addition, using color doppler ultrasound mode, the presence of active microbubbles on the seed is demonstrated by the flashing colours of bubbles breaking under the influence of the ultrasound energy. This energy can be lessened such that the bubbles do not rupture whilst providing a very good image of the seeds themselves.

Example 33

A conventional titanium seed is coated with ECHO-COAT™ using the method described in WO98/19713.

What is claimed is:

1. A medical or surgical device or tool that is a radioactive source suitable for use in brachytherapy that is designed to be implanted or inserted inside the human or mammalian body, having at least part of its' surface coated whereby the ultrasound visibility of said device or tool in vivo is enhanced, characterised in that the coating comprises one or more of the following:

(i) a matrix material containing a plurality of contrast enhancing elements;

(ii) magnesium;

(iii) a liquid or polymer which alters its ultrasound imaging properties upon elevating the temperature from ambient to physiological temperature;

(iv) a liquid or polymer which alters its ultrasound imaging properties as a result of a change in pH;

an essentially non-polymeric bio-compatible compound which forms a discontinuous coating.

2. The coated device or tool as claimed in claim 1 where the surface is an outer surface of the device or tool.

3. The device or tool as claimed in claim 1, where the radioactive source is a seed.

4. The radioactive source as claimed in claim 1 wherein the coating comprises a matrix material containing a plurality of contrast enhancing elements and wherein the contrast enhancing elements comprise one or more of bubbles or microbubbles of a gas or a precursor to a gas, or ultrasound-reflecting particles.

5. The radioactive source as claimed in claim 1 wherein the coating comprises a matrix material and the matrix material comprises a polymer.

6. The radioactive source as claimed in claim 5 wherein the polymer is a polyurethane, polyethylene, polypropylene, poly (ethylene-co-vinyl acetate), partially hydrolyzed poly (ethylene-co-vinyl acetate), poly (ethylene-co-vinyl alcohol), a polysilicone, a polybutylene, polyisoprene, a halogenated rubber, a halogenated elastomer, a polymer or copolymer of a vinyl-alkylene, a polymeric ethylene oxide, a polyether, a polyacrylate, a polyepoxide, a polyacrylamide, a polypeptide, polyvinylpyrrolidone, gelatin, Chemglaze A276, S13GLO, YB-71 or D-11.

7. The radioactive source as claimed in claim 1 wherein the coating comprises a matrix material and the matrix material comprises a fused or melted amino acid or a fused sugar.

8. The radioactive source as claimed in claim 1 wherein the coating comprises a matrix material and the matrix material comprises particles of metal, glass, silica, iron oxide, sand, clay, plastic, or are hollow microcapsules or solid microspheres.

9. The coated device or tool as claimed in claim 1 wherein the coating comprises an essentially non-polymeric biocompatible compound which forms a discountinuous coating and wherein the discontinuous coating comprises biocompatible metal oxide particles, particles of an X-ray contrast agent, entrapped bubbles, phase separate regions, entrapped micro domains, or regions of a biocompatible gaseous substance or precursors to a biocompatible gaseous substance, optionally in the presence of a biocompatible membrane forming material.

10. The coated device or tool as claimed in claim 1 wherein the coating comprises an essentially non-polymeric bio-compatible compound and wherein the essentially non-polymeric biocompatible compound comprises a sugar, an amino acid, a solid iodinated contrast agent, a dextrin or a solid lipid material.

11. The coated device or tool as claimed in claim 1 wherein the coating comprises a polymer which alters its ultrasound imaging properties upon temperature elevation or a change in pH, and the polymer emits a gas from its covalent structure.

12. The coated device or tool as claimed in claim 1 wherein the coating comprises a liquid which alters its ultrasound imaging properties upon temperature elevation, and the liquid comprises a liquid which evaporates at a temperature between ambient and physiological temperature.

13. In a method of preparation of the coated device or tool as claimed in claim 1, wherein the coating comprises an essentially non-polymeric biocompatible compound which forms a discontinuous coating, the improvement comprising providing a composition in powdered form comprising a non-polymeric bio-compatible compound, and fusing said compound to form a coating on the device.

14. The method of claim 13 where the fusing step is carried out in the presence of a bio-compatible gas or a liquid that can become a gas on heating.

15. In a method of preparation of a coated device or tool as claimed in claim 1, wherein the coating comprises magnesium, the improvement comprising applying the coating by vapour deposition or electroplating of magnesium, or dipping the device or tool in molten magnesium.

16. A method for improving the in vitro ultrasound visibility of a radioactive source suitable for use in brachytherapy, which comprises providing at least part of the surface of said source with at least one of the coatings of claim 1.

17. The method of claim 16 wherein the surface is an outer surface.

* * * * *